US009750756B2

(12) United States Patent
Gao et al.

(10) Patent No.: US 9,750,756 B2
(45) Date of Patent: Sep. 5, 2017

(54) CELECOXIB COMPOSITIONS

(71) Applicant: Pfizer Inc., New York, NY (US)

(72) Inventors: Danchen Gao, Chicago, IL (US);
Anthony J. Hlinak, Lindenhurst, IL
(US); Ahmad M. Mazhary, Algonquin,
IL (US); James E. Truelove,
Libertyville, IL (US); Margaret B.
Vaughn, Winnetka, IL (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/493,921

(22) Filed: Sep. 23, 2014

(65) Prior Publication Data

US 2015/0011514 A1   Jan. 8, 2015

Related U.S. Application Data

(63) Continuation of application No. 13/418,852, filed on Mar. 13, 2012, now abandoned, which is a continuation of application No. 09/451,641, filed on Nov. 30, 1999, now abandoned.

(60) Provisional application No. 60/110,333, filed on Nov. 30, 1998.

(51) Int. Cl.
| A61K 9/14 | (2006.01) |
| A61K 31/635 | (2006.01) |
| A61K 9/20 | (2006.01) |
| A61K 9/48 | (2006.01) |
| A61K 31/415 | (2006.01) |
| A61K 9/00 | (2006.01) |
| A61K 45/06 | (2006.01) |
| A61K 9/16 | (2006.01) |

(52) U.S. Cl.
CPC .......... *A61K 31/635* (2013.01); *A61K 9/0053* (2013.01); *A61K 9/2013* (2013.01); *A61K 9/2018* (2013.01); *A61K 9/2027* (2013.01); *A61K 9/2054* (2013.01); *A61K 9/2095* (2013.01); *A61K 9/4858* (2013.01); *A61K 9/4866* (2013.01); *A61K 31/415* (2013.01); *A61K 45/06* (2013.01); *A61K 9/1694* (2013.01)

(58) Field of Classification Search
None
See application file for complete search history.

(56) References Cited

U.S. PATENT DOCUMENTS

| 4,666,705 | A | 5/1987 | DeCrosta et al. |
| 4,681,755 | A | 7/1987 | Colombo et al. |
| 4,786,503 | A | 11/1988 | Edgren et al. |
| 4,814,175 | A | 3/1989 | Tack et al. |
| 4,826,689 | A | * | 5/1989 | Violanto ................ A61K 9/14 210/639 |
| 4,865,849 | A | 9/1989 | Conte et al. |
| 4,871,548 | A | 10/1989 | Edgren et al. |
| 4,882,144 | A | 11/1989 | Hegasy et al. |
| 4,882,169 | A | 11/1989 | Ventouras |
| 4,895,726 | A | 1/1990 | Curtet et al. |
| 4,952,402 | A | 8/1990 | Sparks et al. |
| 4,971,790 | A | 11/1990 | Magruder et al. |
| 5,043,167 | A | 8/1991 | Rotini et al. |
| 5,108,757 | A | 4/1992 | Erdos et al. |
| 5,112,619 | A | 5/1992 | Thakkar et al. |
| 5,264,446 | A | 11/1993 | Hegasy et al. |
| 5,266,581 | A | 11/1993 | Schmidt et al. |
| 5,342,624 | A | 8/1994 | McNeill et al. |
| 5,466,823 | A | 11/1995 | Talley et al. |
| 5,474,784 | A | 12/1995 | Stevens et al. |
| 5,474,995 | A | 12/1995 | Ducharme et al. |
| 5,518,738 | A | 5/1996 | Eickhoff et al. |
| 5,540,669 | A | 7/1996 | Sage et al. |
| 5,543,099 | A | 8/1996 | Zhang et al. |
| 5,552,160 | A | 9/1996 | Liversidge et al. |
| 5,563,165 | A | 10/1996 | Talley et al. |
| 5,591,456 | A | * | 1/1997 | Franson ................ A61K 9/146 424/493 |
| 5,633,272 | A | 5/1997 | Talley et al. |
| 5,643,933 | A | 7/1997 | Talley et al. |
| 5,739,166 | A | 4/1998 | Reitz et al. |
| 5,756,529 | A | 5/1998 | Isakson et al. |
| 5,760,068 | A | 6/1998 | Talley et al. |
| 5,869,096 | A | 2/1999 | Barclay et al. |
| 5,932,576 | A | 8/1999 | Anantanarayan et al. |
| 5,958,452 | A | 9/1999 | Oshlack et al. |
| 6,048,850 | A | 4/2000 | Young et al. |

(Continued)

FOREIGN PATENT DOCUMENTS

CA   EP 0863134 A1 *  9/1998  ........... C07C 317/24
EP        0001247         4/1979

(Continued)

OTHER PUBLICATIONS

AAPS Annual Meeting Contributed Papers Abstracts (AAPS); 1997, 3 pages.*
Karim et al., SC-58635 (celecoxib): a highly selective inhibitor of cyclooxygenase-2. Disposition kinetics in man and identification of its major CYP450 isozyme in its biotransformation, AAPS Annual Meeting Contributed Papers/ Abstracts (1997), p. S-617.
Lane, "Pain management in osteoarthritis: the role of COX-2 inhibitors", Journal of Rheumatology, vol. 24, Supp. 49, pp. 20-24 (1997).

(Continued)

Primary Examiner — Susan Tran
(74) Attorney, Agent, or Firm — A. Dean Olson

(57) ABSTRACT

Pharmaceutical compositions are provided comprising one or more orally deliverable dose units, each comprising particulate celecoxib in an amount of about 10 mg to about 1000 mg in intimate mixture with one or more pharmaceutically acceptable excipients. The compositions are useful in treatment or prophylaxis of cyclooxygenase-2 mediated conditions and disorders.

7 Claims, 2 Drawing Sheets

(56) References Cited

U.S. PATENT DOCUMENTS

| | | | | |
|---|---|---|---|---|
| 6,063,811 A | * | 5/2000 | Hancock | A61K 31/341 514/473 |
| 6,077,539 A | | 6/2000 | Plachetka et al. | |
| 6,165,506 A | | 12/2000 | Jain et al. | |
| 6,232,422 B1 | | 5/2001 | Spitz et al. | |
| 6,440,967 B1 | | 8/2002 | Block et al. | |
| 6,586,458 B1 | | 7/2003 | Plachetka | |

FOREIGN PATENT DOCUMENTS

| | | |
|---|---|---|
| EP | 0256933 | 2/1988 |
| EP | 0330532 | 8/1989 |
| EP | 0488856 | 9/1995 |
| EP | 0863134 | 9/1998 |
| EP | 1049467 | 10/2002 |
| WO | 95/00501 | 1/1995 |
| WO | 95/15316 | 6/1995 |
| WO | 95/18799 | 7/1995 |
| WO | 96/21429 | 7/1996 |
| WO | 96/35414 | 11/1996 |
| WO | 96/37476 | 11/1996 |
| WO | 96/38131 | 12/1996 |
| WO | 97/25979 | 7/1997 |
| WO | 97/44028 | 11/1997 |
| WO | 99/09988 | 3/1999 |
| WO | 00/15195 | 3/2000 |
| WO | 00/48583 | 8/2000 |

OTHER PUBLICATIONS

Parnham, Inflammation: mechanisms and therapeutics, Drug News & Perspectives, vol. 9, pp. 631-639 (1996).
Peck et al., "Tablet formulation and design", In Lieberman, et al., (ed.) Pharmaceutical Dosage Forms: Tablets, 2d ed., vol. 1, pp. 75-130 (1989).
Proudfoot, "Factors influencing bioavailability: factors influencing drug absorption from the gastrointenstinal tract." Pharmaceutics: The Science of Dosage Form Design, AULTON, Ed. (1990).
Rubenstein, Tablets. In AULTON (ed.) Pharmaceutics, The Science of Dosage Form Design, pp. 304-321 (1990).
Welling et al., Pharmaceutical Bioequivalence, pp. 413-314 (1991). Marcel Dekker.
Barkin, "Cancer Pain Treatment Insights", Pharmacotherapy, vol. 17(2), pp. 397-398 (1997).
Lipsky, "COX-2 specific inhibitors: Basic science and clinical implications", Am. J. Med., vol. 106(5B), pp. 1S-2S (1999).
Raskin, "Gastrointestinal effects of nonsteroidal anti-inflammatory activity", Am. J. Med., vol. 106(5B), pp. 3S-12S (1999).
Radebaugh & Ravin, Preformulation, In Remington's Pharmacy, 19th Ed., vol. II, Chapter 83, p. 1449 (1995).
Sarafin, "Drugs used in the treatment of asthma", In Goodman & Gilman's Pharmacological Basis of Therapeutics, 9th Ed., Chapter 28, p. 665 (1996).
Whelton, "Nephrotoxicity of nonsteroidal anti-inflammatory drugs physiologic foundations and clinical implications", Am. J. Med., vol. 106(5B), pp. 13S-24S (1999).
Lipsky and Isakson, "Outcome of specific COX-2 inhibition in rheumatoid arthritis", Journal of Rheumatology, vol. 24, Suppl. 49, pp. 9-14 (1997).
Penning et al, "Synthesis and biological evaluation of the 1,5-diarylpyrazole class of cyclooxygenase-2 inhibitors: identification of 4-[5-(4-methylphenyl)-3-trifluoromethyl)-1H,pyrazol-1-yl]benzenesulfonamide (SC-58635, Celecoxib)", J. Med. Chem., vol. 40, pp. 1347-1365 (1997).
Simon et al., "Preliminary study of the safety and efficacy of SC-58635, a novel cyclooxygenase-2 inhibitor", Arthritis & Rheumatism, vol. 41, pp. 1591-1602 (1998).
Vane, "Towards a better Aspirin", Nature, vol. 367, pp. 215-216 (1994).

Battistini et al., "COX-1 and COX-2: Toward the Development of More Selective NSAIDs", Drug News and Perspectives, vol. 7, pp. 501-512 (1994).
Statutory Declaration of Professor Ian Tucker, dated Jan. 4, 2003.
Römpp Cemie Lexikon, 9. Auflage, Band 3, Georg Thieme Verlag, Stuttgart, 1990; pp. 2368-2370.
Teng et al., "Formulation dependent pharmacokinetics, bioavailability and renal toxicity of a selective cyclooxygenase-1 inhibitor sc-560 in the rat", J. Pharm. Pharmaceut. Sci. (www.ualberta.ca/~csps), vol. 6(2); pp. 205-210 (2003).
Strickley, "Solubilizing Excipients in Oral and Injectable Formulations", Pharmaceutical Research, vol. 21(2), pp. 201-230 (2004).
Davies et al., "Clinical Pharmacokinetics and Pharmacodynamics of Celecoxib—A selective Cyclo-Coxygenase-2 Inhibitor", Clin. Pharmacokinet, vol. 39(3); pp. 225-242 (2000).
Barnett International's Strategies for Improving Solubility, Practical Applications for Examining, Measuring, Predicting and Automating Solubility, Jun. 2-4, 2004, Airport Marriott, Philadelphia, PA (6 pages).
2004 PSG Technical Conference, Current Pharmaceutical Products, What Was Once Novel is Now Standard, Le Jardin, 8440 Highway 27, Woodbridge, Ontario Oct. 26-27, 2004 (8 pages).
Memet Bahar, Experimental Protocol—Crystallization Experiments, Product: Celecoxib; Preparation Date: Mar. 9-Mar. 9, 2004 (5 pages).
Davies et al., "Celecoxib: a new option in the treatment of arthropathies and familial adenomatous polyposis", Expert Opinion on Pharmacotherapy, vol. 2(1); pp. 139-152 (2001).
Declaration of Neal M. Davies dated Nov. 17, 2004.
Declaration of Dr. Tambay Taskin dated Feb. 8, 2006.
Kesten Control and Optimisation of Cement Quality with Laser Diffraction Particle Size Analysis and Dry Dispersion, Sympatec GmbH, D-38678 Clausthal-Zellerfeld, Germany (1997).
Clinical Trial Protocol N49-95-02-006, dated Sep. 6, 1995.
Internal redacted Pfizer document dated Jul. 26, 2007 re: particle size analysis of Arti X 200 mg tablets.
Consultant Agreement re: Clinical Trial N49-95-02-006 dated Sep. 20, 1995.
Barber et al., "A Logical Stepwise Approach to Laser Diffraction Particle Size Distribution Analysis Methods Development and Validation", Pharmaceutical Development and Technology, vol. 3(2); pp. 153-161 (1998).
Pharmaceutical Dosage Forms: Tablets, 2nd Edition, vol. 2, (1990).
Jennings et al., "Particle size measurement: the equivalent spherical diameter", Proc. R. Soc. Lond. A, vol. 419, pp. 137-149 (1988).
U.S. Appl. No. 60/047,535, filed May 22, 1997.
Opposition by the Pharmaceutical Industry Chamber of Bolivia dated Oct. 2000 (English translation).
Rejection by Republic of Colombia dated Mar. 16, 2005 (English translation).
Rejection by Costa Rica dated approx. 2008, later overcome. (English translation).
Opposition filed by Association of Pharmaceutical Laboratories in Ecuador dated Aug. 2000 (English Translation).
Decision by European Patent Office in Appeal No. T0696/05-3302 dated Feb. 5, 2009.
Opposition decision by European Patent Office regarding European Patent No. EP1049467 dated Mar. 30, 2005.
Notice of Opposition by Teva Pharmaceutical Industries Ltd. and supporting documents dated Jul. 8, 2003 regarding European Patent No. EP1049467.
Opposition by Zentiva, k.s.. in Estonia dated Feb. 17, 2010 regarding Patent No. EE 04834.
Affidavit of Neal M. Davies, Ph.D. dated Mar. 2006, regarding Guatemalan Patent Application No. PI-990203 and U.S. Pat. No. 5,563,165.
Final Decision filed in Guatemala ordering the Registry of Intellectual Property to proceed with respective registry regarding PI-1999-0203.
Rejection filed regarding Application No. PI-990203 in Guatemala dated Jun. 16, 2003.

(56) References Cited

OTHER PUBLICATIONS

Administrative Appeal Brief regarding Application No. PI-990203 in response to the Guatemalan Examiner's rejection of Jun. 16, 2003.
Submission in Guatemala dated Apr. 2004.
Israel opposition summations, Jul. 2006 (English translation).
Opposition Decision by Israel Patent Office dated Feb. 28, 2008 (English translation).
Appeal to Set Aside Refusal of Application and Reconsideration to Grant Patent to Philippine AN:1-1999-02951 dated Jul. 28, 2009.
Notice of Appeal by Teva Pharmaceutical Industries Ltd. and Trima Israeli Medical Products Maabarot Ltd., filed in Israel, dated Jun. 5, 2009 (English translation).
Declaration by Neal M. Davies, Ph.D. dated Nov. 10, 2004, filed in the Isreal Opposition.
Response to Statement filed by the Camara de le Industria Farmaceutica, in Venezuela regarding Venezuelan Patent Application No. 1999-002453.
Annulment Action filed in Peru on Jan. 11, 2010.
Decision of Industrial Property Office of the Slovak Republic dated Apr. 26, 2010 regarding Slovak Republic Patent No. SK 283510 (English translation).
Nullity Action filed by Zentiva in Slovak Republic on Jul. 19, 2008 (English translation).
Turkish opposition summary by Fako Ilaclari A.S. (Jun. 18, 2001) (English translation).
Turkish opposition by Professor. Levent Öner dated Jun. 5, 2001 (English translation).
Turkish opposition by Tüm Ekìp İla, A.S. (2001) (English translation).
Turkish opposition by Nobel Ilac Sanayi Ve Ticaret, A.S. dated Jun. 19, 2001 (English translation).
Turkish opposition statement by Fako Ilaclari dated Jun. 18, 2001 (English translation).
Nullity Action for patent SK283510, Jul. 19, 2008 (with English translation).
Annex D1: 1997 AAPS Annual Meeting Contributed Papers Abstracts, Abstract 3469: SC-58635 (Celecoxib): A Highly Selective inhibitor of Cyclooxygenase-2. Disposition Kinetics in Man and Identification of its Major CPY450 Isozyme in its Biotransformation, A. Karim, et al.
Annex D3: Prescription Pharmacy: Dosage Formulation and Pharmaceutical Adjuncts, p. 56 (1963).
Annex D4: Pharmaceutical Dosage Forms: Tablets, vol. 1, pp. 5-6 (1989).
Annex D5: Pharmaceutical Dosage Forms: Tablets, vol. 1, pp. 117-134 (1989).
Annex D7: Decision revoking the European Patent (Article 102(1), (3) EPC), European Patent Office, Mar. 30, 2005.
Adverse Third Party Observation filed by Averell B.Gaspar in Phillippine Patent Application No. 1-1999-02951.
Desai et al., "Gastrointestinal Uptake of Biodegradable Microparticles: Effect of Particle Size", Pharmaceutical Research, vol. 13(12), pp. 1838-1845 (1996).
Florence et al., "Factors Affecting the Oral Uptake and translocation of Polystyrene Nanoparticles: Histological and Analytical Evidence", Journal of Drug Targeting, vol. 3, pp. 65-70 (1995).
Gershanik et al., "Interaction of a Self-Emulsifying Liquid Drug Delivery System with the Everted Rat Intestinal Mucosa as a Function of Droplet Size and Surface Charge", Pharmaceutical Research, vol. 15(6), pp. 863-869 (1998).
Kakoulides et al., "Azocrosslinked poly(acrylic acid) for colonic delivery and adhesion specificity in vitro degradation and preliminary ex vivo bioadhesion studies", Journal of Controlled Release, vol. 54, pp. 95-109 (1998).
Kawamori et al., "Chemopreventive Activity of Celecoxib, a Specific Cyclooxygenase-2 inhibitor against Colon Carcinogenesis", Cancer Research, vol. 58, pp. 409-412 (1998).
Kulvanich et al., "The effect of particle size and concentrating on the adhesive characteristics of a mode drug carrier interactive system", J. Pharm Pharmacol., vol. 39, pp. 673-678 (1987).
McClean et al., "Binding and uptake of biodegradable polylactide micro- and nanoparticles in intestinal epithelia", European Journal of Pharmaceutical Sciences, (website version), vol. 6(2), pp. 153-163 (1998).
Rodriguez et al., "Design of a new multiparticulate system for potential site-specific and controlled drug delivery to the colonic region", Journal of Controlled Release, vol. 55, p. 67-77 (1998).
Rubenstein "Approaches and Opportunities in Colon-Specific Drug Delivery", Critical Reviews in Therapeutic Drug Carrier Systems, vol. 12(2&3), pp. 101-149 (1995).
Smith et al., "Pharmacological analysis of cyclooxygenase-1 in inflammation", Proc. Nat'l. Acad. Sci. USA, vol. 95, pp. 13313-13318 (1998).
Tirosh et al., "Migration of Adhesive and Nonadhesive Particles in the Rate Intestine under Altered Mucus Secretion Conditions", Journal of Pharmaceutical Sciences, vol. 87(4), pp. 453-456 (1998).
Wadke et al., "Performulation testing IV. Particle size, shape and surface area", Pharmaceutical Dosage Forms, Tablets, 2d ed., vol. 1, Ch. 1, pp. 5-6 (1989).
AAPS Annual Meeting Contributed Papers Abstracts, 1997, 3 pages.
Amidon et al., "A theoretical basis for a biopharmaceutic drug classification: the correlation of in vitro drug product dissolution and in vivo bioavailability", Pharmaceutical Research, vol. 12(3), pp. 413-420 (1995).
Aulton ed., Pharmaceutics: The Science of Dosage Form Design, Edinburgh: Churchill Livingstone. Pages cited: 8, 156, 311 and 330 (1988).
Basit et al., "The effect of polyethylene glycol 400 on gastrointestinal transit: implications for the formulation of poorly water-soluble drugs", Pharmaceutical Research, vol. 18(8), pp. 1146-1150 (2001).
Bauer et al., Pharmazeutische Technologie, 3rd Ed., Stuttgart: Verlag. pp. 104, 203 (1991).
Berry & Nash, ed., Pharmaceutical Process Validation, 2d Ed., New York: Marcel Dekker. pp. 174-181 (1993).
British Pharmacopoeia 1993. pp. vol. I, 316; vol. II, 753.
Fincher et al., "Effect of particle size on gastrointestinal absorption of sulfisoxazole in dogs", J. Pharm. Sci., vol. 5495), pp. 704-708 (1965).
Ghosh et al., "Product development studies on the tablet formulation of ibuprofen to improve bioavailability", Drug Development & Industrial Pharmacy, vol. 24(5), pp. 473-477 (1998).
Gibaldi, Biopharmaceutics and Clinical Pharmacokinetics, 4th ed., Philadelphia: Lea & Febiger. pp. 51, 52 and 62 (1991).
Hubbard et al., "SC-58635, a highly selective inhibitor ofCOX-2 is an effective analgesic in an acute non-surgical pain model", J. Invest. Med., vol. 44(3), p. 293A (1996).
Hubbard et al., "SC-58635 (celecoxib), a novel COX-2 selective inhibitor, is effective as a treatment for osteoarthritis (OA) in a short-term pilot study", Arthritis & Rheumatism, vol. 39, Supp. 9, S226, abstract 1188 (1996).
Hubbard et al., "Pilot efficacy of SC-58635, a Cox-2 selective inhibitor, in rheumatoid arthritis", Arthritis & Rheumatism, vol. 40, S51, abstract 125 (1997).
Kaneniwa et al., "Dissolution of slightly soluble drugs. I. Influence of particle size on dissolution behavior", Chem. Pharm. Bull., vol. 22(8), pp. 1699-1705 (1973).
Kaneniwa et al., "Dissolution of slightly soluble drugs. IV. Effect of particle size of sulfonamides on in vitro dissolution rate and in vivo absorption rate, and their relation to solubility", Chem. Pharm. Bull., vol. 26(3), pp. 813-826 (1978).
Lachman et al. (ed.), The Theory and Practice of Industrial Pharmacy, 3rd ed., Philadelphia: Lea & Febiger. pp. 21-45 and 321-328 (1986).
Levy, "Effect of particle size on dissolution and gastrointestinal absorption rates of pharmaceuticals", Am. J. Pharm., pp. 78-92 (Mar. 1963).
List, Arzneiformenlehre, 4th ed., Stuttgart: Wissenschaftliche Verlagegesellschaft, pp. 210, 523. (1985).

(56) References Cited

OTHER PUBLICATIONS

Martin, Physical Pharmacy, 4th ed., Philadelphia: Lea & Febiger. pp. 331, 423-436 (1993).
Ridolfo et al.,"Benoxaprofen, a new anti-inflammatory agent: particle-size effect on dissolution rate and oral absorption in humans", J. Pharm. Sci., vol. 68(7), pp. 850-852 (1979).
Sprowls, Prescription Pharmacy. Philadelphia: Lippincott. pp. 56 (1963).
Voigt, Lehrbuch der Pharmazeutischer Technologie, 5th ed. Basel: Verlag. pp. 471, 472 and 637 (1984).
Wade and Weller, Handbook of Pharmaceutical Excipients, 2d. ed. Washington: American Pharmaceutical Association. pp. v, vi (Contents pages), 141, 163, 252, 280, 433 and 448 (1994).
Wadke et al., Pharmaceutical Dosage Forms: Tablets, 2d ed., "Preformulation testing IV. Particle size, shape and surface area," vol. 1, Ch. 1, pp. 5-6 (1989).
Zhao et al., "Effect of celecoxib, a novel COX-2 inhibitor, on health-related quality of life of patients with osteoarthritis of the knee", Arthritis & Rheumatism, vol. 40 (Supp. 9), S88, abstract 348 (1997).
Abdou, Dissolution, Bioavailability and Bioequivalence, pp. 58-66, 457-458 Mack Publishing Co. (1989).
American Pharmaceutical Association Handbook of Pharmaceutical Excipients, pp. 1-2, 5, 9-11, 26-33, 39-40, 45-48, 53-58, 93-98, 113-115, 119-121, 123-126, 128-129, 134-135, 138-140, 153-162, 166-169, 177-183, 209-211, 214-215, 234-239, 261-262, 266-268, 271-272, 275-278, 284-293, 298-300, 304-308 (1986).
Anon, Drugs of the Future, vol. 22(7), Section headed "Pharmacokinetics", p. 713 (1997).
Bandelin, "Compressed tablets by wet granulation", In Lieberman (ed.) Pharmaceutical Dosage Forms: Tablets, 2d ed., vol. 1, pp. 131-193 (1989).
Banker & Anderson, Tablets. In Lachman et al. (ed.) The Theory and Practice of Industrial Pharmacy, pp. 293-373 (1986).
DiSanto, Bioavailability and Bioequivalency Testing, Chapter 77 in Remington's Pharmaceutical Sciences, 17th ed., pp. 1424-1431 (1985).
Hubbard et al., "Efficacy, tolerability and safety of celecoxib in osteoarthritis", American College of Rheumatology, 62nd National Scientific Meeting, San Diego, CA, Nov. 1998.

\* cited by examiner

CELECOXIB COMPOSITIONS

This application claims the benefit of U.S. provisional application Ser. No. 60/110,333 filed Nov. 30, 1998.

FIELD OF THE INVENTION

The present invention relates to orally deliverable pharmaceutical compositions containing celecoxib as an active ingredient, to processes for preparing such compositions, to methods of treatment of cyclooxygenase-2 mediated disorders comprising orally administering such compositions to a subject, and to the use of such compositions in the manufacture of medicaments.

BACKGROUND OF THE INVENTION

The compound 4-[5-(4-methylphenyl)-3-(trifluoromethyl)-1H-pyrazol-1-yl]benzenesulfonamide (also referred to herein as celecoxib) was previously reported in Talley et al., U.S. Pat. No. 5,466,823 which describes and claims a class of 1,5-diaryl pyrazoles and their salts together with processes for the preparation of such compounds. Celecoxib has the structure:

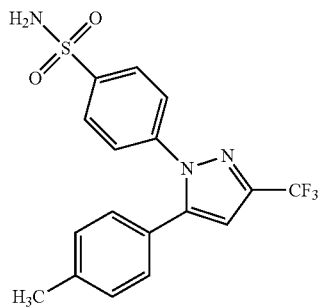

The 1,5-diaryl pyrazole compounds reported in U.S. Pat. No. 5,466,823 are described therein as useful in treating inflammation and inflammation-related disorders. U.S. Pat. No. 5,466,823 contains general references to formulations for the administration of these 1,5-diaryl pyrazoles, including orally deliverable dosage forms such as tablets and capsules. Talley et al, U.S. Pat. No. 5,760,068 reports a class of 1,5-diaryl pyrazole compounds including celecoxib that are described as selective inhibitors of cyclooxygenase-2 and that can be administered to treat, among other conditions and disorders, pathological conditions associated with rheumatoid arthritis and osteoarthritis.

Penning et al., "Synthesis and Biological Evaluation of the 1,5-Diarylpyrazole Class of Cyclooxygenase-2 Inhibitors: Identification of 4-[5-(4-Methylphenyl)-3-(trifluoromethyl)-1H-pyrazol-1-yl]benzenesulfonamide (SC-58635, Celecoxib)", *J. Med. Chem.* 40 (1997):1347-1365, discloses the preparation of a series of sulfonamide-containing 1,5-diarylpyrazole derivatives, including celecoxib, and the evaluation of those derivatives as cyclooxygenase-2 inhibitors.

Simon et al., "Preliminary Study of the Safety and Efficacy of SC-58635, a Novel Cyclooxygenase 2 Inhibitor", *Arthritis & Rheumatism*, Vol. 41, No. 9, September 1998, pp. 1591-1602, discloses a study of the efficacy and safety of celecoxib in the treatment of osteoarthritis and rheumatoid arthritis.

Lipsky et al., "Outcome of Specific COX-2 Inhibition in Rheumatoid Arthritis", *J. Rheumatology*, Vol. 24, Suppl. 49, pp. 9-14 (1997), discloses that in patients with rheumatoid arthritis the specific inhibition of cyclooxygenase-2 by celecoxib is sufficient to suppress signs and symptoms of inflammatory disease activity.

European Patent Application No. 0 863 134 A 1, published Sep. 9, 1998, discloses compositions comprising a cyclooxygenase-2 inhibitor, specifically 2)-3,5-difluorophenyl)-3-(4-methyl-sulfonyl)phenyl)-2-cyclopenten-1-one, in combination with excipient ingredients including microcrystalline cellulose, lactose monohydrate, hydroxypropyl cellulose, croscarmellose sodium and magnesium stearate.

The formulation of celecoxib for effective oral administration to a subject has hitherto been complicated by the unique physical and chemical properties of the compound, particularly its low solubility and factors associated with its crystal structure, including cohesiveness, low bulk density and low compressibility. Celecoxib is unusually insoluble in aqueous media. Unformulated celecoxib is not readily dissolved and dispersed for rapid absorption in the gastrointestinal tract when administered orally, for example in capsule form. In addition, unformulated celecoxib, which has a crystal morphology that tends to form long cohesive needles, typically fuses into a monolithic mass upon compression in a tableting die. Even when blended with other substances, the celecoxib crystals tend to separate from the other substances and agglomerate together during mixing of the composition resulting in a non-uniformly blended composition containing undesirably large aggregates of celecoxib. Therefore, it is difficult to prepare a pharmaceutical composition containing celecoxib that has the desired blend uniformity. Further, handling problems are encountered during the preparation of pharmaceutical compositions comprising celecoxib. For example, the low bulk density of celecoxib makes it difficult to process the small quantities required during formulation of the pharmaceutical compositions. Accordingly, a need exists for solutions to numerous problems associated with preparation of suitable pharmaceutical compositions and dosage forms comprising celecoxib, particularly orally deliverable dose units.

In particular, a need exists for orally deliverable celecoxib formulations possessing one or more of the following characteristics relative to unformulated celecoxib or other celecoxib compositions:

(1) improved solubility;
(2) shorter disintegration time;
(3) shorter dissolution time;
(4) decreased tablet friability;
(5) increased tablet hardness;
(6) improved wettability;
(7) improved compressibility;
(8) improved flow properties of liquid and particulate solid compositions;
(9) improved physical stability of the finished composition;
(10) reduced tablet or capsule size;
(11) improved blend uniformity;
(12) improved dose uniformity;
(13) improved control of weight variation during encapsulation and/or tableting;
(14) increased granule density for wet granulated compositions;
(15) reduced water requirement for wet granulation;
(16) reduced wet granulation time; and
(17) reduced drying time for wet granulated mixtures.

As is indicated hereinbelow, celecoxib treatment is indicated or potentially indicated in a very wide array of cyclooxygenase-2 mediated conditions and disorders. It would therefore be of great benefit to provide a range of formulations having bioavailability characteristics tailored to different indications. It would be of especial benefit to provide formulations exhibiting pharmacokinetics consistent with a more rapid onset effect than is possible with unformulated celecoxib.

Such formulations would represent a significant advance in the treatment of cyclooxygenase-2 mediated conditions and disorders.

SUMMARY OF THE INVENTION

There is now provided a pharmaceutical composition comprising one or more orally deliverable dose units, each comprising particulate celecoxib in an amount of about 10 mg to about 1000 mg in intimate mixture with one or more pharmaceutically acceptable excipients.

In one embodiment, a single dose unit, upon oral administration to a fasting subject, provides a time course of blood serum concentration of celecoxib having at least one of the following:
  (a) a time to reach 100 ng/ml not greater than about 0.5 h after administration;
  (b) a time to reach maximum concentration ($T_{max}$) not greater than about 3 h after administration;
  (c) a duration of time wherein concentration remains above 100 ng/ml not less than about)$_2$ h;
  (d) a terminal half-life ($T_{1/2}$) not less than about 10 h; and
  (e) a maximum concentration ($C_{max}$) not less than about 200 ng/ml.

In another embodiment, the composition has a relative bioavailability not less than about 50% by comparison with an orally delivered solution containing an equivalent amount of celecoxib.

In still another embodiment, the composition has a distribution of celecoxib primary particle sizes such that $D_{90}$ is less than about 200 μm (90% of a sample of particles is smaller than the $D_{90}$ value) in the longest dimension of the particles.

It is to be understood that (a) particular, preferred or illustrative features or properties, (b) particular, preferred or illustrative ingredients, and (c) particular, preferred or illustrative amounts, or ranges of amounts, of such ingredients, disclosed hereinbelow with respect to any of the above embodiments of the invention apply to all of these embodiments.

The dose units comprising the composition can be in the form of discrete solid articles such as tablets, pills, hard or soft capsules, lozenges, sachets or pastilles; alternatively the composition can be in the form of a substantially homogeneous flowable mass, such as a particulate or granular solid or a liquid suspension, from which single dose units are measurably removable.

Also provided is a method of treating a medical condition or disorder in a subject where treatment with a cyclooxygenase-2 inhibitor is indicated, comprising orally administering a composition of the invention once or twice a day.

Other features of this invention will be in part apparent and in part pointed out hereinafter.

DETAILED DESCRIPTION OF THE INVENTION

Figure 1:
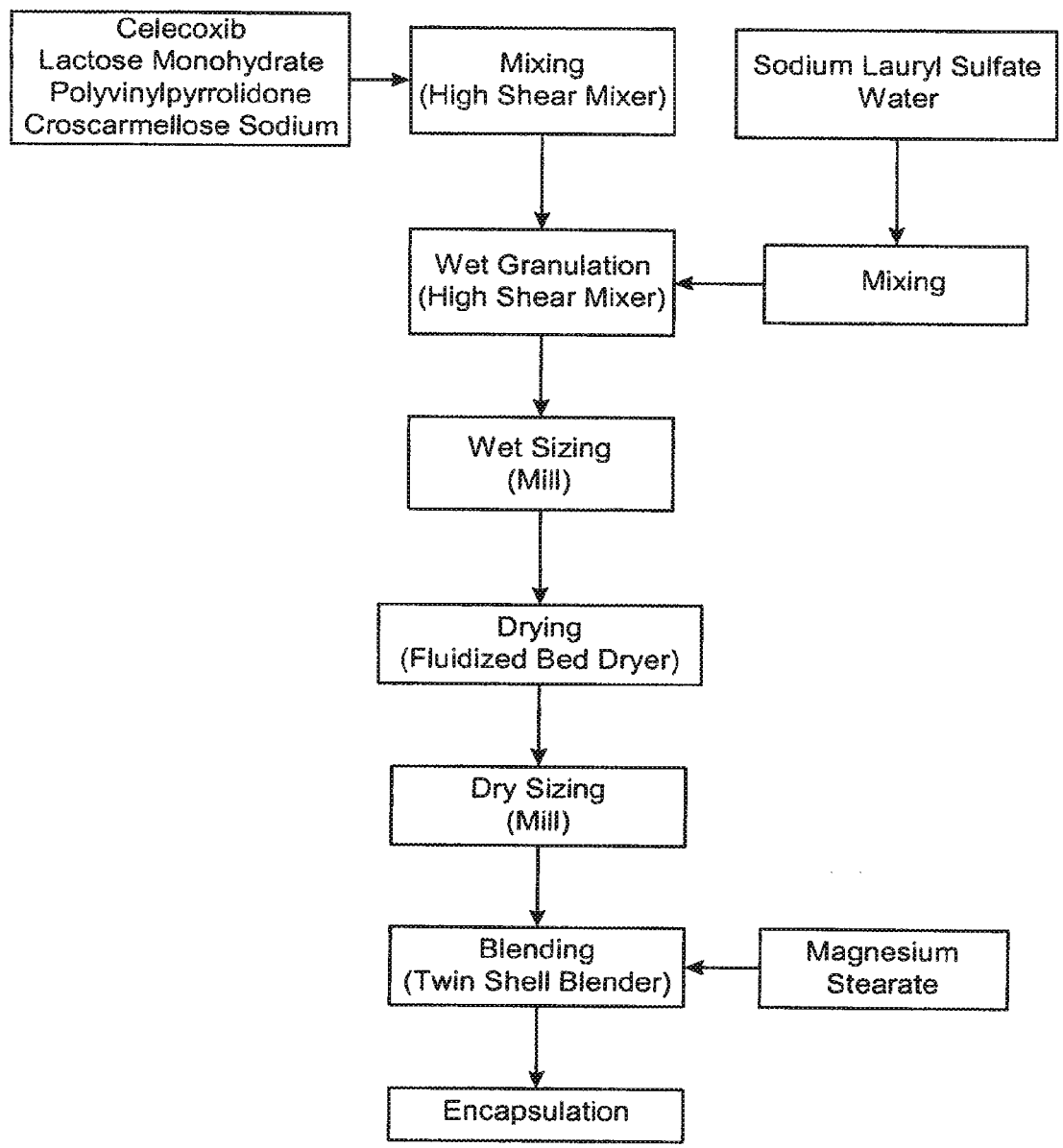
FIG. 1 is a flow diagram illustrating a representative method for the preparation of pharmaceutical compositions of the present invention in the form of capsules.

Novel pharmaceutical compositions according to the present invention comprise one or more orally deliverable dose units, wherein each dose unit comprises particulate celecoxib in an amount from about 10 mg to about 1000 mg and are superior immediate release compositions capable of providing rapid relief from a cyclooxygenase-2 mediated disorder when orally administered to a subject suffering from such a disorder.

It is believed, without being bound by theory, that the strong clinical benefits afforded by these compositions result from improved bioavailability of celecoxib, in particular from surprisingly effective absorption of celecoxib in the gastrointestinal tract. Such effective absorption can be verified by one of skill in the art by monitoring blood serum concentration of celecoxib in a treated subject for a period of time following administration. It is desired to reach, in as short a time as possible, a threshold of celecoxib concentration in the blood serum consistent with effective cyclooxygenase-2 inhibition, without having that concentration subsequently decrease too rapidly so that the beneficial effects of the celecoxib can be maintained for as long a time as possible.

In one embodiment of the invention, therefore, each orally deliverable dose unit, upon oral administration, provides a time course of blood serum concentration of celecoxib characterized by at least one of the following:
  (a) a time to reach a blood serum concentration of about 100 ng/ml that is not greater than about 0.5 hour after administration;
  (b) a time to reach a maximum blood serum concentration ($T_{max}$) of celecoxib that is not greater than about 3 hours after administration, preferably not greater than about 2 hours after administration;
  (c) a duration of time wherein the blood serum concentration remains above about 100 ng/ml that is not less than about 12 hours;
  (d) a terminal half life ($T_{in}$) that is not less than about 10 hours; and
  (e) a maximum blood serum concentration ($C_{max}$) that is not less than about 200 ng/ml, preferably not less than about 300 ng/ml, and more preferably not less than about 400 ng/ml.

It will be understood that the amount of celecoxib in a dose unit effective to provide blood serum concentrations meeting any of criteria (a) to (e) immediately above is dependent on the body weight of the treated subject. Where the subject is a child or a small animal (e.g., a dog), for example, an amount of celecoxib relatively low in the indicated range of about 10 mg to about 1000 mg is likely to provide blood serum concentrations consistent with at least one of criteria (a) to (e). Where the subject is an adult human or a large animal (e.g., a horse), the indicated blood serum concentrations of celecoxib are likely to require dose units containing a relatively greater amount of celecoxib. For an adult human, a suitable amount of celecoxib per dose unit in a composition of the present invention to provide the indicated blood serum concentrations is typically about 75 mg to about 400 mg.

Bioavailability of orally delivered celecoxib in an absolute sense is difficult to measure, because intravenous delivery (normally the standard against which such bioavailability is determined) is highly problematical with a drug having very low solubility in water, as is the case with celecoxib. Relative bioavailability is, however, determinable by comparison with an orally administered solution of celecoxib in a suitable solvent. It has been found that surprisingly high relative bioavailability is obtainable with orally delivered compositions of the present invention. Thus in one embodiment of the invention, each orally deliverable dose unit, upon oral administration, has a relative bioavailability of not less than about 50%, preferably not less than about 70%, by comparison with an orally delivered solution of celecoxib containing an equivalent amount of celecoxib. As indicated hereinbelow, bioavailability is derived from an integrated measure of blood serum concentration of celecoxib over a period of time following oral administration.

Compositions of the present invention contain celecoxib in particulate form. Primary celecoxib particles, generated for example by milling or grinding, or by precipitation from solution, can agglomerate to form secondary aggregate particles. The term "particle size" as used herein refers to size, in the longest dimension, of primary particles, unless the context demands otherwise. Particle size is believed to be an important parameter affecting the clinical effectiveness of celecoxib. Thus in another embodiment, compositions of the present invention have a distribution of celecoxib particle sizes such that $D_{90}$ of the particles, in their longest dimension, is less than about 200 µm, preferably less than about 100 µm, more preferably less than about 75 µm, even more preferably less than about 40 µm, and most preferably less than about 25 µm. A decrease in particle size of celecoxib in accordance with this embodiment of the invention generally improves the bioavailability of the celecoxib.

In addition or alternatively, celecoxib particles in a composition of the invention preferably have a mean particle size of about 1 µm to about 10 µm, most preferably about 5 µm to about 7 µm.

It has been discovered that milling the celecoxib in an impact mill, such as a pin mill, prior to mixing the celecoxib with excipients to form a composition of the invention, is not only effective in providing improved bioavailability but is also beneficial in overcoming problems associated with the cohesive nature of celecoxib crystals during such mixing or blending. Celecoxib milled using a pin mill is less cohesive than, and does not agglomerate into secondary aggregates of celecoxib particles during blending as readily as, unmilled celecoxib or celecoxib milled using other types of mills, such as fluid energy mills. Reduced agglomeration enables a high degree of blend uniformity, which is of particular importance in formulation of unit dosage forms such as capsules and tablets. This result is particularly unexpected given the utility of fluid energy mills such as air jet mills in preparing other pharmaceutical compounds for formulation. Without being held to a particular theory, it is hypothesized that impact milling modifies the crystal morphology of celecoxib from long needles to a more uniform crystal shape more suitable for blending purposes, whereas the long needles have a greater tendency to survive an air jet milling process.

It has also been discovered that blend uniformity is further improved by wet granulating celecoxib with the carrier materials to prepare the pharmaceutical composition, particularly when the celecoxib starting material used has been impact milled. Impact milling the celecoxib starting material such that particle sizes are as described above, followed by wet granulation, is particularly desirable.

In yet another embodiment, the novel pharmaceutical compositions of the invention comprise celecoxib together with one or more carrier materials or excipients selected from diluents, disintegrants, binding agents, wetting agents and lubricants. Preferably at least one of the carrier materials is a water soluble diluent or wetting agent. Such a water soluble diluent or wetting agent assists in the dispersion and dissolution of the celecoxib when the pharmaceutical composition is ingested. Preferably both a water soluble diluent and a wetting agent are present. A composition of the invention can be a substantially homogeneous flowable mass such as a particulate or granular solid or a liquid, or it can be in the form of discrete articles such as capsules or tablets each comprising a single dose unit.

In a composition that is a substantially homogeneous flowable mass, single dose units are measurably removable using a suitable volumetric measuring device such as a spoon or cup. Suitable flowable masses include, but are not limited to, powders and granules. Alternatively, the flowable mass can be a suspension having the celecoxib in a solid particulate phase dispersed in a liquid phase, preferably an aqueous phase. In preparing such a suspension, use of a wetting agent such as polysorbate 80 or the like is likely to be beneficial. A suspension can be prepared by dispersing milled celecoxib in the liquid phase; alternatively the celecoxib can be precipitated from solution in a solvent such as an alcohol, preferably ethanol. The aqueous phase preferably comprises a palatable vehicle such as water, syrup or fruit juice, for example apple juice.

Utility of Compositions of the Invention

Compositions of the present invention are useful in treatment and prevention of a very wide range of disorders mediated by cyclooxygenase-2. Presently contemplated compositions are useful for, but not limited to, the treatment of inflammation in a subject, as an analgesic for example in the treatment of pain and headaches, and as an antipyretic in the treatment of fever. For example, such compositions are useful to treat arthritic disorders, including but not limited to rheumatoid arthritis, spondyloarthropathies, gouty arthritis, osteoarthritis, systemic lupus erythematosus and juvenile arthritis. Such compositions are also useful in the treatment of asthma, bronchitis, menstrual cramps, preterm labor, tendinitis, bursitis, allergic neuritis, cytomegalovirus infectivity, apoptosis including HIV-induced apoptosis, lumbago, liver disease including hepatitis, skin-related conditions such as psoriasis, eczema, acne, UV damage, burns and dermatitis, and post-operative inflammation including that following ophthalmic surgery such as cataract surgery or refractive surgery. Contemplated compositions are useful to treat gastrointestinal conditions such as inflammatory bowel disease, Crohn's disease, gastritis, irritable bowel syndrome and ulcerative colitis. Contemplated compositions are useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like. Contemplated compositions are useful in the treatment of ophthalmic diseases, such as retinitis, conjunctivitis, retinopathies, uveitis, ocular photophobia, and of acute injury to the eye tissue. Contemplated compositions are useful in the treatment of pulmonary inflammation, such as that associated with viral infections and cystic fibrosis, and in bone resorption such as that associated with osteoporosis. Contemplated compositions are useful for the treatment of certain central nervous system disorders, such as cortical dementias including Alzheimer's disease, neurodegeneration, and central nervous system damage resulting from stroke, ischemia and trauma. The term "treatment" in the present context includes partial or total inhibition of dementias, including Alzheimer's disease, vascular dementia, multi-infarct dementia, pre-senile dementia, alcoholic dementia, and senile dementia.

Compositions of the invention are especially useful as anti-inflammatory agents, such as for the treatment of arthritis, with the additional benefit of having significantly less harmful side effects than compositions of conventional nonsteroidal anti-inflammatory drugs (NSAIDs).

Contemplated compositions are useful in the treatment of allergic rhinitis, respiratory distress syndrome, endotoxin shock syndrome, and liver disease. Contemplated compositions are useful in the treatment of pain, including but not limited to postoperative pain, dental pain, muscular pain, and pain resulting from cancer.

Contemplated compositions are useful for, but not limited to, treating and preventing inflammation-related cardiovascular disorders in a subject. Such compositions are useful for treatment and prevention of vascular diseases, coronary artery disease, aneurysm, vascular rejection, arteriosclerosis, atherosclerosis including cardiac transplant atherosclerosis, myocardial infarction, embolism, stroke, thrombosis including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries. Such compositions are useful for, but not limited to, the treatment of angiogenesis-related disorders in a subject. Compositions of the invention can be administered to a subject in need of angiogenesis inhibition. Such compositions are useful for the treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis.

Contemplated compositions are useful for the prevention or treatment of benign and malignant tumors/neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. Neoplasias for which compositions of the invention are contemplated to be particularly useful are gastrointestinal cancer, Barrett's esophagus, liver cancer, bladder cancer, pancreas cancer, ovary cancer, prostate cancer, cervical cancer, lung cancer, breast cancer and skin cancer, such as squamous cell and basal cell cancers. Compositions of the invention can also be used to treat the fibrosis which occurs with radiation therapy. Such compositions can be used to treat subjects having adenomatous polyps, including those with familial adenomatous polyposis (FAP). Additionally, such compositions can be used to prevent polyps from forming in patients at risk of FAP.

Compositions of the present invention possess anti-inflammatory, antipyretic and analgesic properties similar or superior to those of compositions of conventional nonsteroidal anti-inflammatory drugs. Contemplated compositions also inhibit hormone-induced uterine contractions and have potential anti-cancer effects, but with a diminished ability to induce some of the mechanism-based side effects of conventional NSAIDs. In particular, compositions of the invention have reduced potential for gastrointestinal toxicity and gastrointestinal irritation including upper gastrointestinal ulceration and bleeding, reduced potential for renal side effects such as reduction in renal function leading to fluid retention and exacerbation of hypertension, reduced effect on bleeding times including inhibition of platelet function, and possibly a lessened ability to induce asthma attacks in aspirin-sensitive asthmatic subjects, by comparison with compositions of conventional NSAIDs.

Contemplated compositions are useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, and injuries following surgical and dental procedures. In addition, contemplated compositions inhibit cellular neoplastic transformations and metastic tumor growth and hence can be used in the treatment of cancer, such as cancer of the colon. Contemplated compositions are also of use in the treatment and/or prevention of cyclooxygenase-mediated proliferative disorders such as may occur in diabetic retinopathy and tumor angiogenesis.

Contemplated compositions inhibit prostanoid-induced smooth muscle contraction by preventing the synthesis of contractile prostanoids and hence can be of use in the treatment of dysmenorrhea, premature labour, asthma and eosinophil-related disorders. They also can be of use in the treatment of Alzheimer's disease, for decreasing bone loss particularly in postmenopausal women (i.e., treatment of osteoporosis), and for treatment of glaucoma.

By virtue of their high cyclooxygenase-2 (COX-2) inhibitory activity and/or their specificity for inhibition of cyclooxygenase-2 over cyclooxygenase-1 (COX-1), compositions of the invention are useful as an alternative to conventional NSAIDs, particularly where such NSAIDs are contraindicated, for example in patients with peptic ulcers, gastritis, regional enteritis, ulcerative colitis, diverticulitis or with a recurrent history of gastrointestinal lesions; gastrointestinal bleeding, coagulation disorders including anemia such as hypoprothrombinemia, hemophilia or other bleeding problems; kidney disease; or in patients prior to surgery or patients taking anticoagulants. A brief description of the potential utility of cyclooxygenase-2 inhibitors is given in an article by John Vane, *Nature*, Vol. 367, pp. 215-216, 1994, and in an article in *Drug News and Perspectives*, Vol. 7, pp. 501-512, 1994.

Preferred uses for the pharmaceutical compositions of the present invention are for the treatment of rheumatoid arthritis and osteoarthritis, for pain management generally (particularly post-oral surgery pain, post-general surgery pain, post-orthopedic surgery pain, and acute flares of osteoarthritis), the treatment of Alzheimer's disease, and colon cancer chemoprevention.

Besides being useful for human treatment, compositions of the invention are also useful for veterinary treatment of companion animals, exotic animals and farm animals, and the like, particularly mammals including rodents. More particularly, compositions of the invention are useful for veterinary treatment of cyclooxygenase-2 mediated disorders in horses, dogs, and cats.

The present compositions can be used in combination therapies with opioids and other analgesics, including narcotic analgesics, Mu receptor antagonists, Kappa receptor antagonists, non-narcotic (i.e. non-addictive) analgesics, monamine uptake inhibitors, adenosine regulating agents, cannabinoid derivatives, Substance P antagonists, neurokinin-1 receptor antagonists and sodium channel blockers, among others. Preferred combination therapies comprise use of a composition of the invention with compounds selected from morphine, meperidine, codeine, pentazocine, buprenorphine, butorphanol, dezocine, meptazinol, hydrocodone, oxycodone, methadone, DuP-747, Dynorphine A, Enadoline, RP-60180, ITN-11608, E-2078, ICI-204448, acetaminophen (paracetamol), propoxyphene, nalbuphine, E-4018, filenadol, mirfentanil, amitriptyline, DuP-631, GP-531, acadesine, AKI-1, AKI-2, GP-1683, GP-3269, 4030W92, tramadol racemate and isolated (+) and (−) enantiomers, AXC-3742, SNX-111, ADL2-1294, CT-3, and CP-99994.

Definitions

The term "active ingredient" herein means celecoxib unless the context demands otherwise.

The term "excipient" herein includes any substance used as a vehicle for delivery of the active ingredient to a subject, and any substance added to the active ingredient, for example to improve its handling properties or to permit the resulting composition to be formed into an orally deliverable unit dose having the desired shape and consistency. Excipients can include, by way of illustration and not by limitation, diluents, disintegrants, binding agents, adhesives, wetting agents, lubricants, glidants, substances added to mask or counteract a bad taste or odor, flavors, dyes, substances added to improve appearance of a dosage form, and any other substance other than the active ingredient conventionally used in the preparation of oral dosage forms.

The term "adjuvant" herein means a substance that, when present in or added to a pharmaceutical composition comprising an active ingredient, increases or otherwise improves the action of the active ingredient.

The term "unit dose" herein refers to an amount of active ingredient intended for a single oral administration to a subject for treatment or prevention of a cyclooxygenase-2 mediated condition or disorder. Treatment of a cyclooxygenase-2 mediated disorder may require periodic administration of unit doses of celecoxib, for example one unit dose two or more times a day, one unit dose with each meal, one unit dose every four hours or other interval, or only one unit dose per day.

The term "dose unit" herein means a portion of a pharmaceutical composition that contains a single unit dose of the active ingredient. For purposes of the present invention, a dose unit can be in the form of a discrete article such as a tablet or capsule, or can be a measurable volume of a solution, suspension or the like containing a unit dose of the active ingredient.

The term "orally deliverable" herein means intended to be administered to the gastrointestinal tract of a subject via the mouth of said subject.

The term "substantially homogeneous", when used herein to describe a pharmaceutical composition that contains a combination of components, means that the components are fully mixed no that the individual components are neither separated into discrete layers nor form concentration gradients within the composition.

The term "bioavailability" herein relates to a measure of the amount of active ingredient that is absorbed via the gastrointestinal tract into the bloodstream. More specifically, "bioavailability" is used herein to denote $AUC_{(0-\infty)}$ for a specific orally administered composition expressed as a percentage of $AUC_{(0-\infty)}$ for the active ingredient delivered intravenously at the same dosage rate.

The term "relative bioavailability" herein denotes $AUC_{(0-\infty)}$ for a specific orally administered composition expressed as a percentage of $AUC_{(0-\infty)}$ for an orally administered solution of the active ingredient at the same dosage rate.

The terms "$AUC_{(0-24)}$", "$AUC_{(0-48)}$" and "$AUC_{(0-72)}$" herein mean the area under the curve relating blood serum concentration to time after administration from 0 to 24 hours, 48 hours or 72 hours respectively, as determined using the linear trapezoidal rule, and are expressed in units of (ng/ml)h.

The term "$AUC_{(0-LQC)}$" herein means the area under the curve relating blood serum concentration to time after administration from 0 hours to the time of last quantifiable concentration ("LQC"), as determined using the linear trapezoidal rule, and is expressed in units of (ng/ml)h.

The term "$AUC_{(0-\infty)}$" herein is calculated as $AUC_{(0-LQC)}$+LQC/(−b), where LQC is the last quantifiable blood serum concentration and b is the slope from the calculation of $T_{1/2}$, and is expressed in units of (ng/ml)h.

The term "$AUC_{max}$" herein means the maximum observed blood serum concentration or the maximum blood serum concentration calculated or estimated from a concentration/time curve, and is expressed in units of ng/ml.

The term "$T_{max}$" herein means the time after administration at which $C_{max}$ occurs, and is expressed in units of hours (h).

The term "$T_{1/2}$" herein means the terminal half-life of blood serum concentration, determined via simple linear regression of natural log(ln) concentration vs. time for data points in the terminal phase of the concentration-time curve. $T_{1/2}$ is computed as $-\ln(2)/(-b)$ and is expressed in units of hours (h).

The term "rate of absorption" herein means $C_{max}/AUC_{(0-LQC)}$.

Celecoxib Dosage Provided by Compositions of the Invention

The pharmaceutical compositions of the present invention are suitable for administration of celecoxib in a daily dosage amount from about 10 mg to about 1000 mg. Each dose unit of a composition of the invention typically comprises an amount of celecoxib from about one-tenth of the daily dosage amount to the whole of a daily dosage amount. Compositions of the invention comprise celecoxib in an amount of about 10 mg to about 1000 mg, preferably about 50 mg to about 800 mg, more preferably about 75 mg to about 400 mg, and most preferably about 100 mg to about 200 mg, per dose unit. Where the dose units are in the form of discrete articles suitable for oral administration, for example capsules or tablets, each such article comprises about 10 mg to about 1000 mg, preferably about 50 mg to about 800 mg, more preferably about 75 mg to about 400 mg, and most preferably about 100 mg to about 200 mg, of celecoxib.

Dose units of compositions of the invention typically contain, for example, a 10, 20, 25, 37.5, 50, 75, 100, 125, 150, 175, 200, 250, 300, 350 or 400 mg dose of celecoxib. Preferred compositions have dose units containing about 100 mg or about 200 mg of celecoxib. The particular dose unit can be selected to accommodate the desired frequency of administration used to achieve a desired daily dosage. The daily dosage and frequency of administration, and therefore the selection of appropriate dose unit, depends on a variety of factors, including the age, weight, sex and medical condition of the subject, and the nature and severity of the condition or disorder, and thus may vary widely.

It has been discovered, however, that a once-a-day or twice-a-day administration regimen to provide the required daily dosage of celecoxib exhibits improved efficacy relative to other administration regimens, for compositions illustrated herein. Accordingly, once-a-day or twice-a-day oral administration of a composition of the invention is preferred for providing therapeutically or prophylatically effective inhibition of cyclooxygenase-2 mediated disorders.

Treatment of Specific Conditions and Disorders

The pharmaceutical compositions of the present invention are useful where administration of a cyclooxygenase-2 inhibitor is indicated. It has been found that these compositions are particularly effective in the treatment of, for example, rheumatoid arthritis and osteoarthritis, and for pain management generally (particularly post-oral surgery pain, post-general surgery pain, post-orthopedic surgery pain, and acute flares of osteoarthritis), the treatment of Alzheimer's disease, and colon cancer chemoprevention.

For the treatment of rheumatoid arthritis, compositions of the invention can be used to provide a daily dosage of celecoxib of about 50 mg to about 1000 mg, preferably about 100 mg to about 600 mg, more preferably about 150 mg to about 500 mg, and still more preferably about 175 to about 400, for example about 200 mg. A daily dose of celecoxib of about 0.67 to about 13.3 mg/kg body weight, preferably about 1.33 to about 8.00 mg/kg body weight, more preferably about 2.00 to about 6.67 mg/kg body weight, and still more preferably about 2.33 to about 5.33 mg/kg body weight, for example about 2.67 mg/kg body weight, is generally appropriate when administered in a composition of the invention. The daily dose can be administered in one to four doses per day, preferably one or two doses per day. Administration of a composition of the invention at the rate of one 100 mg dose unit twice a day is preferred for most patients, but some patients may benefit from administration of one 200 mg dose unit or two 100 mg dose units twice a day.

For the treatment of osteoarthritis, compositions of the invention can be used to provide a daily dosage of celecoxib of about 50 mg to about 1000 mg, preferably about 100 mg to about 600 mg, more preferably about 150 mg to about 500 mg, and still more preferably about 175 to about 400, for example about 200 mg. A daily dose of celecoxib of about 0.67 to about 13.3 mg/kg body weight, preferably about 1.33 to about 8.00 mg/kg body weight, more preferably about 2.00 to about 6.67 mg/kg body weight, and still more preferably about 2.33 to about 5.33 mg/kg body weight, for example about 2.67 mg/kg body weight, is generally appropriate when administered in a composition of the invention. The daily dose can be administered in one to four doses per day, preferably one or two doses per day. Administration of a composition of the invention at the rate of one 100 mg dose unit twice a day or of one 200 mg dose unit or two 100 mg dose units once a day is preferred.

For the treatment of Alzheimer's disease, compositions of the invention can be used to provide a daily dosage of celecoxib of about 50 mg to about 1000 mg, preferably about 100 mg to about 800 mg, more preferably about 150 mg to about 600 mg, and still more preferably about 175 to about 400, for example about 400 mg. A daily dose of about 0.67 to about 13.3 mg/kg body weight, preferably about 1.33 to about 10.67 mg/kg body weight, more preferably about 2.00 to about 8.00 mg/kg body weight, and still more preferably about 2.33 to about 5.33 mg/kg body weight, for example about 5.33 mg/kg body weight, is generally appropriate when administered in a composition of the invention. The daily dose can be administered in one to four doses per day, preferably one or two doses per day. Administration of a composition of the invention at the rate of one 200 mg dose unit or two 100 mg dose units twice a day is preferred for most patients.

For the treatment of cancer, compositions of the invention can be used to provide a daily dosage of celecoxib of about 50 mg to about 1000 mg, preferably about 100 mg to about 800 mg, more preferably about 150 mg to about 600 mg, and still more preferably about 175 to about 400, for example about 400 mg. A daily dose of about 0.67 to about 13.3 mg/kg body weight, preferably about 1.33 to about 10.67 mg/kg body weight, more preferably about 2.00 to about 8.00 mg/kg body weight, and still more preferably about 2.33 to about 5.33 mg/kg body weight, for example about 5.33 mg/kg body weight, is generally appropriate when administered in a composition of the invention. The daily dose can be administered in one to four doses per day, preferably two doses per day, Administration of a composition of the invention at the rate of one 200 mg dose unit or two 100 mg dose units twice a day is preferred for most patients.

In general, a composition of the invention is preferably administered at a dose suitable to provide an average blood serum concentration of celecoxib of at least about 100 ng/ml in a subject over a period of about 24 hours after administration.

It has been found that the pharmaceutical compositions of the present invention provide a therapeutic effect as cyclooxygenase-2 inhibitors over an interval of about 12 to about 24 hours after oral administration. Preferred compositions provide such therapeutic effect over about 24 hours, enabling once-a-day oral administration.

While the amount of celecoxib in the novel compositions of the invention preferably is in a range disclosed herein, the compositions also may be useful for the administration of an amount of celecoxib falling outside the disclosed dosage ranges.

Preparation of Celecoxib

The celecoxib used in the novel pharmaceutical compositions of the present invention can be prepared in the manner set forth in Talley et al., U.S. Pat. No. 5,466,823, or in Zhi et al., WO 96/37476.

Form of Compositions of the Invention

The pharmaceutical compositions of the present invention comprise celecoxib in association with one or more preferably non-toxic, pharmaceutically acceptable carriers, excipients and adjuvants (collectively referred to herein as "carrier materials" or "excipients") suitable for oral administration. The carrier materials must be acceptable in the sense of being compatible with the other ingredients of the composition and must not be deleterious to the recipient. Compositions of the present invention can be adapted for administration by any suitable oral route by selection of appropriate carrier materials and a dosage of celecoxib effective for the treatment intended. Accordingly, any carrier materials employed can be solids or liquids, or both, and the composition preferably contains about 1% to about 95%, preferably about 10% to about 90%, more preferably about 25% to about 85%, and still more preferably about 30% to about 80%, by weight of celecoxib. Such pharmaceutical compositions of the invention can be prepared by any of the well known techniques of pharmacy, comprising admixing the components.

A composition of the invention contains a desired amount of celecoxib per dose unit and can be in the form of, for example, a tablet, a pill, a hard or soft capsule, a lozenge, a cachet, a dispensable powder, granules, a suspension, an elixir, a liquid, or any other form reasonably adapted for oral administration. Such a composition is preferably made in the form of discrete dose units each containing a predetermined amount of celecoxib, such as tablets or capsules. These oral dosage forms may further comprise, for example, buffering agents. Tablets, pills and the like additionally can be prepared with or without coatings.

Compositions of the invention suitable for buccal or sublingual administration include, for example, lozenges comprising celecoxib in a flavored base, such as sucrose, and acacia or tragacanth, and pastilles comprising celecoxib in an inert base such as gelatin and glycerin or sucrose and acacia.

Liquid dosage forms for oral administration include pharmaceutically acceptable suspensions, syrups, and elixirs containing inert diluents commonly used in the art, such as water. Such compositions may also comprise, for example, wetting agents, emulsifying and suspending agents, and sweetening, flavoring, and perfuming agents.

As indicated above, compositions of the invention can be prepared by any suitable method of pharmacy which includes the step of bringing into association the celecoxib and the carrier material or carrier materials. In general, the compositions are prepared by uniformly and intimately admixing celecoxib with a liquid or finely divided solid carrier, or both, and then, if necessary, encapsulating or shaping the product. For example, a tablet can be prepared by compressing or molding a powder or granules of the compound, together with one or more excipients. Compressed tablets can be prepared by compressing, in a suitable machine, a free-flowing composition, such as a powder or granules, comprising celecoxib optionally mixed with one or more binding agent(s), lubricant(s), inert diluent(s), wetting agent(s) and/or dispersing agent(s). Molded tablets can be made by molding, in a suitable machine, the powdered compound moistened with an inert liquid diluent.

Carrier Materials or Excipients

As noted above, the pharmaceutical compositions of the present invention comprise celecoxib in a therapeutically or prophylactically effective amount per dose unit in combination with one or more pharmaceutically acceptable carrier materials appropriate for oral administration, Compositions of the present invention preferably comprise celecoxib in a desired amount admixed with one or more carrier materials selected from the group consisting of pharmaceutically acceptable diluents, disintegrants, binding agents, adhesives, wetting agents, lubricants, and anti-adherent agents. More preferably, such compositions are tableted or encapsulated for convenient administration in the form of immediate release capsules or tablets.

Through the selection and combination of carrier materials used in the pharmaceutical compositions of the present invention, compositions can be provided exhibiting improved performance with respect to, among other properties, efficacy, bioavailability, clearance time, stability, compatibility of celecoxib and carrier materials, safety, dissolution profile, disintegration profile and/or other pharmacokinetic, chemical and/or physical properties. The carrier materials preferably are water soluble or water dispersible and have wetting properties to offset the low aqueous solubility and hydrophobicity of celecoxib. Where the composition is formulated as a tablet, the combination of carrier materials selected provides tablets that can exhibit improvement, among other properties, in dissolution and disintegration profiles, hardness, crushing strength, and/or friability.

Diluents

The pharmaceutical compositions of the present invention optionally comprise one or more pharmaceutically acceptable diluents as a carrier material. Suitable diluents include, either individually or in combination, lactose USP; lactose USP, anyhydrous; lactose USP, spray dried; starch USP; directly compressible starch; mannitol USP; sorbitol; dextrose monohydrate; microcrystalline cellulose NF; dibasic calcium phosphate dihydrate NF; sucrose-based diluents; confectioner's sugar; monobasic calcium sulfate monohydrate; calcium sulfate dihydrate NF; calcium lactate trihydrate granular NF; dextrates, NF (e.g., Emdex); Celutab; dextrose (e.g., Cerelose); inositol; hydrolyzed cereal solids such as the Maltrons and Mor-Rex; amylase; Rexcel; powdered cellulose (e.g., Elcema); calcium carbonate; glycine; bentonite; polyvinylpyrrolidone; and the like. Such diluents, if present, constitute in total about 5% to about 99%, preferably about 10% to about 85%, and more preferably about 20% to about 80%, of the total weight of the composition. The diluent or diluents selected preferably exhibit suitable flow properties and, where tablets are desired, compressibility.

Lactose and microcrystalline cellulose, either individually or in combination, are preferred diluents. Both diluents are chemically compatible with celecoxib. The use of extragranular microcrystalline cellulose (that is, microcrystalline cellulose added to a wet granulated composition after the drying step) can be used to improve hardness (for tablets) and/or disintegration time. Lactose, especially lactose monohydrate, is particularly preferred. Lactose typically provides pharmaceutical compositions having suitable celecoxib release rates, stability, pre-compression flowability, and/or drying properties at a relatively low diluent cost. It provides a high density substrate that aids densification during granulation (where wet granulation is employed) and therefore improves blend flow properties.

Disintegrants

The pharmaceutical compositions of the present invention optionally comprise one or more pharmaceutically acceptable disintegrants as a carrier material, particularly for tablet formulations. Suitable disintegrants include, either individually or in combination, starches; sodium starch glycolate; clays (such as Veegum HV); celluloses (such as purified cellulose, methylcellulose, sodium carboxymethylcellulose and carboxymethylcellulose); alginates; pregelatinized corn starches (such as National 1551 and National 1550); crospovidone USP NF; and gums (such as agar, guar, locust bean, Karaya, pectin, and tragacanth). Disintegrants may be added at any suitable step during the preparation of the pharmaceutical composition, particularly prior to granulation or during the lubrication step prior to compression. Such disintegrants, if present, constitute in total about 0.2% to about 30%, preferably about 0.2% to about 10%, and more preferably about 0.2% to about 5%, of the total weight of the composition.

Croscarmel lose sodium is a preferred disintegrant for tablet or capsule disintegration, and, if present, preferably constitutes about 0.2% to about 10%, more preferably about 0.2% to about 6%, and still more preferably about 0.2% to about 5%, of the total weight of the composition. Croscarmellose sodium confers superior intragranular disintegration capabilities to compositions of the present invention.

Binding Agents and Adhesives

The pharmaceutical compositions of the present invention optionally comprise one or more pharmaceutically-acceptable binding agents or adhesives as a carrier material, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starch; cellulose materials such as, but not limited to, methylcellulose and sodium carboxymethylcellulose (e.g., Tylose); alginic acid and salts of alginic acid; magnesium aluminum silicate; polyethylene glycol; guar gum; polysaccharide acids; bentonites; polyvinylpyrrolidone; polymethacrylates; hydroxypropylmethylcellulose (HPMC); hydroxypropylcellulose (Klucel); ethylcellulose (Ethocel); pregelatinized starch (such as National 1511 and Starch 1500). Such binding agents and/or adhesives, if present, constitute in total about 0.5% to about 25%, preferably about 0.75% to about 15%, and more preferably about 1% to about 10%, of the total weight of the composition.

Polyvinylpyrrolidone is a preferred binding agent used to impart cohesive properties to a powder blend of celecoxib and other excipients for granulation of a celecoxib formulation. Polyvinylpyrrolidone, if present, preferably constitutes about 0.5% to about 10%, more preferably about 0.5% to about 7%, and still more preferably about 0.5% to about 5% of the total weight of the composition. Polyvinylpyrrolidone viscosities up to about 20 cPs may be used although viscosities of about 6 cPs or lower are preferred, particularly about 3 cPs or lower. Polyvinylpyrrolidone provides cohesiveness to the powder blend and facilitates the necessary binding to form granules during wet granulation. In addition, compositions of the present invention comprising polyvinylpyrrolidone, particularly compositions prepared by wet granulation, have been found to exhibit improved bioavailability relative to other compositions.

Wetting Agents

Celecoxib is largely insoluble in aqueous solution. Accordingly, the pharmaceutical compositions of the present invention optionally but preferably comprise one or more pharmaceutically acceptable wetting agents as a carrier material. Such wetting agents are preferably selected to maintain celecoxib in close association with water, a condition that is believed to improve the relative bioavailability of the pharmaceutical composition. Suitable wetting agents include, either individually or in combination, oleic acid; glyceryl monostearate; sorbitan monooleate; sorbitan monolaurate; triethanolamine oleate; polyoxyethylene sorbitan monooleate; polyoxyethylene sorbitan monolaurate; sodium oleate; and sodium lauryl sulfate. Wetting agents that are anionic surfactants are preferred. Such wetting agents, if present, constitute in total about 0.25% to about 15%, preferably about 0.4% to about 10%, and more preferably about 0.5% to about 5%, of the total weight of the composition.

Sodium lauryl sulfate is a preferred wetting agent. Sodium lauryl sulfate, if present, constitutes about 0.25% to about 7%, more preferably about 0.4% to about 6%, and still more preferably about 0.5 to about 5% of the total weight of the composition.

Lubricants

The pharmaceutical compositions of the present invention optionally comprise one or more pharmaceutically acceptable lubricants and/or glidants as a carrier material. Suitable lubricants and/or glidants include, either individually or in combination, glyceryl behapate (Compritol 888); stearates (magnesium, calcium, and sodium); stearic acid; hydrogenated vegetable oils (e.g., Sterotex); talc; waxes; Stearowet; boric acid; sodium benzoate; sodium acetate; sodium fumarate; sodium chloride; DL-leucine; polyethylene glycols (e.g., Carbowax 4000 and Carbowax 6000); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the composition.

Magnesium stearate is a preferred lubricant used, for example, to reduce friction between the equipment and granulated mixture during compression of tablet formulations.

Other carrier materials (such as anti-adherent agents, colorants, flavors, sweeteners and preservatives) are known in the pharmaceutical art and can be included in compositions of the present invention. For example, iron oxide can be added to the composition to provide a yellow color.

Capsules and Tablets

In one embodiment of the present invention, the pharmaceutical composition is in the form of unit dose capsules or tablets and comprises celecoxib in a desired amount and a binding agent. The composition preferably further comprises one or more carrier materials selected from the group consisting of pharmaceutically acceptable diluents, disintegrants, binding agents, wetting agents, and lubricants. More preferably, the composition comprises one or more carrier materials selected from the group consisting of lactose, sodium lauryl sulfate, polyvinylpyrrolidone, croscarmellose sodium, magnesium stearate, and microcrystalline cellulose. Still more preferably, the composition comprises lactose monohydrate and croscarmellose sodium. Still more preferably, the composition further comprises one or more of the carrier materials sodium lauryl sulfate, magnesium stearate, and microcrystalline cellulose.

In another embodiment, the pharmaceutical composition comprises:

(a) about 1 to about 95 weight percent of celecoxib;
(b) about 5 to about 99 weight percent of a pharmaceutically acceptable diluent;
(c) about 0.5 to about 30 weight percent of a pharmaceutically acceptable disintegrant; and
(d) about 0.5 to about 25 weight percent of a pharmaceutically acceptable binding agent.

In addition, this pharmaceutical composition optionally comprises:

(e) about 0.25 to about 15 weight percent of a pharmaceutically acceptable wetting agent; and/or
(f) about 0.1 to about 10 weight percent of a pharmaceutically acceptable lubricant.

The term "weight percent" as used herein means the weight percent of a specified ingredient based upon the total weight of all ingredients of the composition.

In another embodiment, the pharmaceutical composition comprises:
- (a) about 1 to about 95 weight percent of celecoxib;
- (b) about 5 to about 99 weight percent of lactose;
- (c) about 2 to about 6 weight percent of croscarmellose sodium; and
- (d) about 0.5 to about 10 weight percent of polyvinylpyrrolidone.

In addition, this pharmaceutical composition optionally comprises:
- (e) about 0.25 to about 7 weight percent of sodium lauryl sulfate;
- (f) about 0.1 to about 10 weight percent of magnesium stearate; and/or
- (g) about 1 to about 99 weight percent of microcrystalline cellulose.

In another embodiment, the pharmaceutical composition comprises:
- (a) about 80 to about 220 mg of celecoxib;
- (b) about 30 to about 225 mg of lactose;
- (c) about 0.5 to about 25 mg of croscarmellose sodium; and
- (d) about 0.5 to about 25 mg of polyvinylpyrrolidone.

In addition, this pharmaceutical composition optionally comprises.
- (e) about 0.5 to about 25 mg of sodium lauryl sulfate;
- (f) about 0.2 to about 10 mg of magnesium stearate; and/or
- (g) about 1 mg to about 70 mg of microcrystalline cellulose.

In another embodiment, the pharmaceutical composition comprises:
- (a) about 25 to about 85 weight percent of celecoxib;
- (b) about 5 to about 70 weight percent of lactose;
- (c) about 0.2 to about 5 weight percent of croscarmellose sodium; and
- (d) about 0.5 to about 7 weight percent of polyvinylpyrrolidone.

In addition, this pharmaceutical composition optionally comprises:
- (e) about 0.4 to about 6 weight percent of sodium lauryl sulfate;
- (f) about 0.2 to about 8 weight percent of magnesium stearate; and/or
- (g) about 0.1 to about 15 weight percent of microcrystalline cellulose.

The composition of this embodiment preferably is in the form of a unit dosage capsule.

In another embodiment, the pharmaceutical composition comprises:
- (a) about 27 to about 47 weight percent of celecoxib;
- (b) about 45 to about 65 weight percent of lactose;
- (c) about 0.5 to about 5 weight percent of croscarmellose sodium; and
- (d) about 0.5 to about 5 weight percent of polyvinylpyrrolidone.

In addition, this pharmaceutical composition optionally comprises:
- (e) about 0.25 to about 7 weight percent of sodium lauryl sulfate; and/or
- (f) about 0.25 to about 5 weight percent of magnesium stearate.

The composition of this embodiment preferably is in the form of a unit dosage capsule. In this embodiment, the pharmaceutical composition preferably comprises:
- (a) about 32 to about 42 weight percent of celecoxib;
- (b) about 50 to about 60 weight percent of lactose;
- (c) about 0.5 to about 3 weight percent of croscarmellose sodium; and
- (d) about 1 to about 5 weight percent of polyvinylpyrrolidone.

In addition, this pharmaceutical composition optionally comprises:
- (e) about 0.4 to about 6 weight percent of sodium lauryl sulfate; and/or
- (f) about 0.5 to about 3 weight percent of magnesium stearate.

In this embodiment, the pharmaceutical composition more preferably comprises:
- (a) about 35 to about 39 weight percent of celecoxib;
- (b) about 54 to about 57 weight percent of lactose;
- (c) about 0.5 to about 2 weight percent of croscarmellose sodium; and
- (d) about 1.5 to about 4.5 weight percent of polyvinylpyrrolidone.

In addition, this pharmaceutical composition optionally comprises:
- (e) about 2 to about 4 weight percent of sodium lauryl sulfate; and/or
- (f) about 0.5 to about 2 weight percent of magnesium stearate.

In another embodiment, the pharmaceutical composition comprises:
- (a) about 65 to about 85 weight percent of celecoxib;
- (b) about 8 to about 28 weight percent of lactose;
- (c) about 0.5 to about 5 weight percent of croscarmellose sodium; and
- (d) about 0.5 to about 5 weight percent of polyvinylpyrrolidone.

In addition, this pharmaceutical composition optionally comprises:
- (e) about 0.25 to about 7 weight percent of sodium lauryl sulfate; and/or
- (f) about 0.25 to about 5 weight percent of magnesium stearate.

The composition of this embodiment preferably is in the form of a unit dosage capsule. In this embodiment, the pharmaceutical composition preferably comprises:
- (a) about 69 to about 79 weight percent of celecoxib;
- (b) about 13.5 to about 23.5 weight percent of lactose;
- (c) about 0.5 to about 3 weight percent of croscarmellose sodium; and
- (d) about 1 to about 5 weight percent of polyvinylpyrrolidone.

In addition, this pharmaceutical composition optionally comprises:
- (e) about 0.4 to about 6 weight percent of sodium lauryl sulfate; and/or
- (f) about 0.5 to about 3 weight percent of magnesium stearate.

In this embodiment, the pharmaceutical composition more preferably comprises:
- (a) about 72 to about 76 weight percent of celecoxib;
- (b) about 16.5 to about 20.5 weight percent of lactose;
- (c) about 0.5 to about 2 weight percent of croscarmellose sodium; and
- (d) about 1.5 to about 4.5 weight percent of polyvinylpyrrolidone.

In addition, this pharmaceutical composition optionally comprises:
(e) about 2 to about 4 weight percent of sodium lauryl sulfate; and/or
(f) about 0.5 to about 2 weight percent of magnesium stearate.

In another embodiment, the pharmaceutical composition comprises:
(a) about 30 to about 50 weight percent of celecoxib;
(b) about 30 to about 50 weight percent of lactose;
(c) about 0.5 to about 6 weight percent of croscarmellose sodium; and
(d) about 0.5 to about 5 weight percent of polyvinylpyrrolidone.

In addition, this pharmaceutical composition optionally comprises:
(e) about 1 to about 20 weight percent of microcrystalline cellulose;
(f) about 0.25 to about 7 weight percent of sodium lauryl sulfate; and/or
(g) about 0.25 to about 5 weight percent of magnesium stearate.

The composition of this embodiment preferably is in the form of a unit dosage tablet. In this embodiment, the pharmaceutical composition preferably comprises:
(a) about 35 to about 45 weight percent of celecoxib;
(b) about 35 to about 45 weight percent of lactose;
(c) about 1 to about 5 weight percent of croscarmellose sodium; and
(d) about 1 to about 5 weight percent of polyvinylpyrrolidone.

In addition, this pharmaceutical composition optionally comprises:
(e) about 5 to about 15 weight percent of microcrystalline cellulose;
(f) about 0.4 to about 6 weight percent of sodium lauryl sulfate; and/or
(g) about 0.5 to about 3 weight percent of magnesium stearate.

In this embodiment, the pharmaceutical composition more preferably comprises:
(a) about 38 to about 42 weight percent of celecoxib;
(b) about 38 to about 42 weight percent of lactose;
(c) about 1.5 to about 4.5 weight percent of croscarmellose sodium; and
(d) about 1.5 to about 4.5 weight percent of polyvinylpyrrolidone.

In addition, this pharmaceutical composition optionally comprises:
(e) about 8 to about 12 weight percent of microcrystalline cellulose;
(f) about 2 to about 4 weight percent of sodium lauryl sulfate; and/or
(g) about 0.5 to about 2 weight percent of magnesium stearate.

In another embodiment, the pharmaceutical composition comprises:
(a) about 95 to about 105 mg of celecoxib;
(b) about 145 to about 155 mg of lactose monohydrate;
(c) about 0.5 to about 8 mg of croscarmellose sodium; and
(d) about 2 to about 12 mg of polyvinylpyrrolidone.

In addition, this pharmaceutical composition optionally comprises:
(e) about 3 to about 13 mg of sodium lauryl sulfate; and/or
(f) about 0.5 to about 8 mg of magnesium stearate.

The composition of this embodiment preferably is in the form of a unit dosage capsule. In this embodiment, the pharmaceutical composition preferably comprises:
(a) about 98 to about 102 mg of celecoxib;
(b) about 148 to about 152 mg of lactose monohydrate;
(c) about 1.5 to about 4.5 mg of croscarmellose sodium; and
(d) about 4.5 to about 8.5 mg of polyvinylpyrrolidone.

In addition, this pharmaceutical composition optionally comprises:
(e) about 6 to about 10 mg of sodium lauryl sulfate; and/or
(f) about 1 to about 5 mg of magnesium stearate.

In another embodiment, the pharmaceutical composition comprises:
(a) about 195 to about 205 mg of celecoxib;
(b) about 45 to about 55 mg of lactose monohydrate;
(c) about 0.5 to about 8 mg of croscarmellose sodium; and
(d) about 2 to about 12 mg of polyvinylpyrrolidone.

In addition, this pharmaceutical composition optionally comprises:
(e) about 3 to about 13 mg of sodium lauryl sulfate; and/or
(f) about 0.5 to about 8 mg of magnesium stearate.

The composition of this embodiment preferably is in the form of a unit dosage capsule. In this embodiment, the pharmaceutical composition preferably comprises:
(a) about 198 to about 202 mg of celecoxib;
(b) about 48 to about 52 mg of lactose monohydrate;
(c) about 1.5 to about 4.5 mg of croscarmellose sodium; and
(d) about 4.5 to about 8.5 mg of polyvinylpyrrolidone.

In addition, this pharmaceutical composition optionally comprises:
(e) about 6 to about 10 mg of sodium lauryl sulfate; and/or
(t) about 1 to about 5 mg of magnesium stearate.

In another embodiment, the pharmaceutical composition comprises:
(a) about 95 to about 105 mg of celecoxib;
(b) about 92 to about 112 mg of lactose monohydrate;
(c) about 2 to about 13 mg of croscarmellose sodium; and
(d) about 1 to about 11 mg of polyvinylpyrrolidone.

In addition, this pharmaceutical composition optionally comprises:
(e) about 20 to about 30 mg of microcrystalline cellulose;
(f) about 3 to about 13 mg of sodium lauryl sulfate; and/or
(g) about 0.5 to about 7 mg of magnesium stearate.

The composition of this embodiment preferably is in the form of a unit dosage tablet. In this embodiment, the pharmaceutical composition preferably comprises:
(a) about 98 to about 102 mg of celecoxib;
(b) about 100 to about 104 mg of lactose monohydrate;
(c) about 5 to about 10 mg of croscarmellose sodium; and
(d) about 4 to about 8.5 mg of polyvinylpyrrolidone.

In addition, this pharmaceutical composition optionally comprises:
(e) about 23 to about 27 mg of microcrystalline cellulose;
(f) about 5 to about 10 mg of sodium lauryl sulfate; and/or
(g) about 0.5 to about 4 mg of magnesium stearate.

In another embodiment, the pharmaceutical composition comprises:
(a) about 195 to about 205 mg of celecoxib;
(b) about 199 to about 209 mg of lactose monohydrate;
(c) about 10 to about 20 mg of croscarmellose sodium; and
(d) about 7.5 to about 17.5 mg of polyvinylpyrrolidone.

In addition, this pharmaceutical composition optionally comprises:

(e) about 45 to about 55 mg of microcrystalline cellulose;
(f) about 10 to about 20 mg of sodium lauryl sulfate; and/or
(g) about 0.5 to about 9 mg of magnesium stearate.

The composition of this embodiment preferably is in the form of a unit dosage tablet. In this embodiment, the pharmaceutical composition preferably comprises:

(a) about 98 to about 102 mg of celecoxib;
(b) about 202 to about 206 mg of lactose monohydrate;
(c) about 13 to about 17 mg of croscarmellose sodium; and
(d) about 10.5 to about 14.5 mg of polyvinylpyrrolidone.

In addition, this pharmaceutical composition optionally comprises:

(e) about 48 to about 52 mg of microcrystalline cellulose;
(f) about 13 to about 17 mg of sodium lauryl sulfate; and/or
(g) about 2 to about 6 mg of magnesium stearate.

Celecoxib Particle Size in Capsules and Tablets

It has been discovered that reduction of celecoxib particle size can improve celecoxib bioavailability when administered orally in the form of capsules or tablets. Accordingly, the $D_{90}$ particle size of the celecoxib preferably is less than about 200 μm, more preferably less than about 100 μm, still more preferably less than about 75 μm, still more preferably less than about 40 μm, and most preferably less than about 25 μm. For example, as illustrated in Example 11, reducing the $D_{90}$ particle size of the starting material celecoxib from about 60 μm to about 30 μm can materially improve the bioavailability of the composition. In addition or alternatively, the celecoxib preferably has a mean particle size in the range of about 1 μm to about 10 μm, more preferably about 5 μm to about 7 μm.

Granulation Secondary Particle Size and Flow Properties

Although the pharmaceutical compositions of the present invention can be prepared, for example, by direct encapsulation or direct compression, they preferably are wet granulated prior to encapsulation or compression. Wet granulation, among other effects, densies milled compositions resulting in improved flow properties, improved compression characteristics and easier metering or weight dispensing of the compositions for encapsulation or tableting. The secondary particle size resulting from granulation (i.e., granule size) is not narrowly critical, it being important only that the average granule size preferably is such as to allow for convenient handling and processing and, for tablets, to permit the formation of a directly compressible mixture that forms pharmaceutically acceptable tablets.

The desired tap and bulk densities of the granules are normally about 0.3 g/ml to about 1.0 g/ml.

Release Profile of Capsules and Tablets

Capsule and tablet compositions of the present invention preferably are immediate release compositions that release at least about 50% of the celecoxib, as measured in vitro, within about 45 minutes of ingestion. More preferably, they release at least about 60% of the celecoxib within about 45 minutes of ingestion. Still more preferably, they release at least about 75% of the celecoxib within about 45 minutes of ingestion.

Especially preferred capsule and tablet compositions of the invention release at least about 50% of the celecoxib within about 15 minutes of ingestion, and/or at least about 60% of the celecoxib within about 30 minutes after ingestion.

Disintegration Profile of Capsules and Tablets

Carrier materials for immediate release capsule and tablet compositions of the invention preferably are selected to provide a disintegration time of less than about 30 minutes, preferably about 25 minutes or less, more preferably about 20 minutes or less, and still more preferably about 15 minutes or less.

Hardness

For tablet formulations, the complete mixture in an amount sufficient to make a uniform batch of tablets is subjected to tableting in a conventional production scale tableting machine at normal compression pressure (for example, applying a force of about 1 kN to about 50 kN in a typical tableting die). Any tablet hardness convenient with respect to handling, manufacture, storage and ingestion may be employed. For 100 mg tablets, hardness is preferably at least 4 kP, more preferably at least about 5 kP, and still more preferably at least about 6 kP. For 200 mg tablets, hardness is preferably at least 7 kP, more preferably at least about 9 kP, and still more preferably at least about 11 kP. The mixture, however, is not to be compressed to such a degree that there is subsequent difficulty in achieving hydration when exposed to gastric fluid.

Friability

For tablet formulations, tablet friability preferably is less than about 1.0%, more preferably less than 0.8%, and still more preferably less than about 0.5% in a standard test.

Method of Treatment

The present invention also is directed to a therapeutic method of treating a condition or disorder where treatment with a cyclooxygenase-2 inhibitor is indicated, the method comprising oral administration of a pharmaceutical composition of the present invention to a patient in need thereof. The dosage regimen to prevent, give relief from, or ameliorate the condition or disorder preferably corresponds to the once-a-day or twice-a-day treatments discussed above, but can be modified in accordance with a variety of factors. These include the type, age, weight, sex, diet, and medical condition of the patient and the nature and severity of the disorder. Thus, the dosage regimen actually employed can vary widely and can therefore deviate from the preferred dosage regimens set forth above.

Initial treatment of a patient suffering from a condition or disorder where treatment with a cyclooxygenase-2 inhibitor is indicated can begin with the dosages indicated above. Treatment is generally continued as necessary over a period of several weeks to several months or years until the condition or disorder has been controlled or eliminated. Patients undergoing treatment with a composition of the invention can be routinely monitored by any of the methods well known in the art to determine the effectiveness of therapy. Continuous analysis of such data permits modification of the treatment regimen during therapy so that optimally effective amounts of celecoxib are administered at any point in time, and so that the duration of treatment can be determined as well. In this way, the treatment regimen/dosing schedule can be rationally modified over the course of therapy so that the lowest amount of celecoxib exhibiting satisfactory effectiveness is administered, and so that administration is continued only so long as is necessary to successfully treat the condition or disorder.

Methods for Preparation of Celecoxib Compositions

The present invention also is directed to methods for the preparation of pharmaceutical compositions comprising celecoxib. In particular, the invention is directed to methods for preparing pharmaceutical compositions comprising celecoxib in particulate form. More particularly, the invention is directed to methods for preparing celecoxib compositions in the form of discrete unit dose tablets or capsules, such that each tablet or capsule contains an amount of celecoxib sufficient to provide a therapeutic effect for about 12 to 24 hours. Each dose unit preferably contains, for example, about 100 mg to about 200 mg of celecoxib. According to the present invention, wet granulation, dry granulation or direct compression or encapsulation methods can be employed to prepare tablet or capsule compositions of the invention.

Wet granulation is a preferred method of preparing pharmaceutical compositions of the present invention. In the wet granulation process, celecoxib (if desired, together with one or more carrier materials) is initially milled or micronized to the desired particle size. Although various conventional mills or grinders can be used, impact milling such as pin milling of the celecoxib provides improved blend uniformity to the final composition relative to other types of milling. Cooling of the celecoxib, for example, using liquid nitrogen, may be necessary during milling to avoid heating the celecoxib to undesirable temperatures. As previously discussed, reduction of the $D_{90}$ particle size during this milling step to less than about 200 μm, preferably less than about 100 μm, more preferably less than about 75 μm, still more preferably less than about 40 μm, and most preferably less than about 25 μm, can materially increase the bioavailability of the celecoxib.

The milled or micronized celecoxib is then blended, for example in a high shear mixer/granulator, planetary mixer, twin-shell blender or sigma mixer, with one or more carrier materials, including carrier materials milled together with the celecoxib, to form a dry powder mixture. Typically, the drug is blended with one or more diluent(s), disintegrant(s) and/or binding agent(s) and, optionally, one or more wetting agent(s) in this step, but alternatively all or a portion of one or more of the carrier materials can be added in a later step. For example, in tablet formulations where croscarmellose sodium is employed as a disintegrant, it has been discovered that addition of a portion of the croscarmellose sodium during the blending step (providing intragranular croscarmellose sodium) and addition of the remaining portion after the drying step discussed below (providing extragranular croscarmellose sodium) can improve disintegration of the tablets produced. In this situation, preferably about 60% to about 75% of the croscarmellose sodium is added intragranularly and about 25% to about 40% of the croscarmellose sodium is added extragranularly. Similarly, for tablet formulations it has been discovered that addition of microcrystalline cellulose after the drying step below (extragranular microcrystalline cellulose) can improve compressibility of the granules and hardness of the tablets prepared from the granules.

This blending step of the process preferably comprises blending of celecoxib, lactose, polyvinylpyrrolidone and croscarmellose sodium. It has been discovered that blending times as short as three minutes can provide a dry powder mixture having a sufficiently uniform distribution of celecoxib. For example, the dry powder mixtures used in the preparation of 100 mg dose capsules (1080 kg total batch size) and 200 mg dose capsules (918 kg total batch size), respectively, had celecoxib concentrations exhibiting measured relative standard deviation values of 3.6% or less and 1.1% or less, respectively.

Water, preferably purified water, is then added to the dry powder mixture and the mixture is blended for an additional period of time, to form a wet granulated mixture. Preferably a wetting agent is used, and this is preferably first added to the water and mixed for at least 15 minutes, preferably at least 20 minutes, prior to adding the water to the dry powder mixture. The water can be added to the mixture at once, gradually over a period of time, or in several portions over a period of time. The water preferably is added gradually over a period of time. Alternatively, the wetting agent can be added to the dry powder mixture and water then can be added to the resulting mixture.

For the illustrative 100 mg dose capsules (1080 kg batch), for example, water addition rates of about 5 to about 25 kg/minute, preferably about 7 to about 20 kg/minute, and still more preferably about 8 to about 18 kg/minute, provide suitable results. An additional period of mixing after the water addition is complete is preferred to ensure the uniform distribution of the water in the mixture. For this illustrative batch additional mixing times of about 2 to about 10 minutes, preferably about 3 to about 9 minutes, and more preferably about 3 to about 7 minutes, provide suitable results. The wet granulated mixture of this batch preferably comprises about 2% to about 15%, more preferably about 4% to about 12%, and still more preferably about 6% to about 10%, water by weight.

For the illustrative 200 mg dose capsules (918 kg batch), for example, water addition rates of about 5 to about 25 kg/minute, preferably about 7 to about 23 kg/minute, and still more preferably about 8 to about 21 kg/minute, provide suitable results. An additional period of mixing after the water addition is complete is preferred to ensure the uniform distribution of the water in the mixture. For this illustrative batch additional mixing times of about 2 to about 15 minutes, preferably about 3 to about 12 minutes, and more preferably about 3 to about 10 minutes, provide suitable results. The wet granulated mixture of this batch preferably comprises about 2% to about 15%, more preferably about 6% to about 14%, and still more preferably about 8% to about 13%, water by weight.

The wet granulated mixture preferably is then wet milled, for example with a screening mill, to eliminate large agglomerations of material that form as a by-product of the wet granulation operation. If not removed, these agglomerations would prolong the subsequent fluidized bed drying operation and increase the variation with respect to moisture control. For the illustrative 100 mg dose capsules (1080 kg batch) and 200 mg dose capsules (918 kg batch), for example, suitable granulations can be obtained using feed rates up to about 50%, preferably about 2% to about 30%, and still more preferably about 5% to about 20%, of maximum feed rate.

The wet granulated or wet milled mixture is then dried, for example, in an oven or a fluidized bed dryer, preferably a fluidized bed drier, to form dry granules. If desired, the wet granulated mixture can be extruded or spheronized prior to drying. For the drying process, conditions such as inlet air temperature and drying time are adjusted to achieve the desired moisture content for the dry granules. It may be desirable to combine two or more granulation sections for this drying step and subsequent processing steps.

For the illustrative 100 mg dose capsules (1080 kg batch) or 200 mg dose capsules (918 kg batch) discussed above, dryer inlet temperature can be fixed at 60° C. although other inlet temperatures can be used, preferably in the range of about 50° C. to about 70° C. Air flow rate can be varied in the range of about 1000 to about 8000 cubic feet per minute, preferably about 2000 to about 7000 cubic feet per minute, and more preferably about 4000 to about 7000 cubic feet per minute, with a damper opening of about 10% to about 90%, preferably about 20% to about 80%, and still more preferably about 30% to about 70%. Dryer loads of about 35% to about 100%, preferably about 50% to about 100%, and still more preferably about 90% to about 100%, can be used. Average loss on drying of dry granules prepared under these conditions is generally about 0.1% to about 2.0% by weight.

To the extent necessary, the dry granules are then reduced in size in preparation for compression or encapsulation. Conventional particle size reduction equipment such as oscillators or impact mills (such as Fitz mills) can be employed. For the illustrative 100 mg dose capsules (1080 kg batch), for example, suitable granule size reduction can be obtained using feed rates of about 20% to about 70%, preferably about 30% to about 60%; mill speeds of about 20% to about 70%, preferably about 40% to about 60%; and screen sizes of about 0.020 inch (0.5 mm) to about 0.070 inch (1.7 mm), preferably about 0.028 inch (0.7 mm) to about 0.040 inch (1.0 mm). For the illustrative 200 mg dose capsules (918 kg batch), for example, suitable granulations can be obtained using feed rates of about 10% to about 70%, preferably about 20% to about 60%; mill speeds of about 20% to about 60%, preferably about 30% to about 50%; and screen sizes of about 0.020 inch (0.5 mm) to about 0.080 inch (1.9 mm), preferably about 0.028 inch (0.7 mm) to about 0.063 inch (1.6 mm). Smaller screen sizes such as 0.028 inch (0.7 mm), however, were observed to result in lower throughput of product. Larger screen sizes such as 0.063 inch (1.6 mm) resulted in an increased population of granules larger in size than 850 μm. Screen sizes around about 0.040 inch (1.0 mm) appear to eliminate an excessive population of granules larger in size than 850 μm without significantly decreasing throughput.

Variation of the wet granulation and wet milling parameters discussed above can be employed to adjust granule size distributions. For example, a slight decrease in granule size has been observed as mixing time increases for mixtures containing lower water amounts. It is hypothesized that where the water concentration is too low to fully activate the binding agent employed, the cohesive forces between the primary particles within the granules are insufficient to survive the shearing forces generated by the mixing blades and granule size attrition rather than growth occurs. Conversely, increasing the amount of water to fully activate the binding agent allows cohesive forces between the primary particles to survive the shearing forces generated by the mixing blades and granule growth rather than attrition occurs with increased mixing time and/or water addition rate. Variation of the screen size of the wet mill tends to have a greater impact on the granule size than variation of the feed rate and/or mill speed.

The dry granules are then placed in a suitable blender, such as a twin-shell blender, and optionally a lubricant (such as magnesium stearate) and any additional carrier materials are added (such as extragranular microcrystalline cellulose and/or extragranular croscarmellose sodium in certain tablet formulations) to form a final blended mixture. Blending times depend in part upon the process equipment employed. For the 100 mg dose capsules and 200 mg dose capsules (1080 kg and 918 kg batches) discussed above, blending times of at least about 5 minutes at blender loads ranging from about 15% to about 60% and blender rotational speeds of at least about 10 revolutions per minute consistently provided a blended material that was extremely uniform with respect to celecoxib concentration. The relative standard deviations measured for unit dose blend samples were 3.9% or less and 2.2% or less for the 100 mg and 200 mg dose capsules, respectively. Where the diluents include microcrystalline cellulose, the addition of a portion of the microcrystalline cellulose during this step has been found to materially increase granule compressibility and tablet hardness. In addition, increasing the amount of magnesium stearate above about 1% to about 2% was observed to decrease tablet hardness and increase friability and dissolution time.

This final blended mixture is then encapsulated (or, if tablets are to be prepared, compressed into tablets of the desired weight and hardness using appropriately sized tooling). Conventional compression and encapsulation techniques known to those of ordinary skill in the art can be employed. Suitable results have been obtained for capsules by employing bed heights ranging from about 20 mm to about 60 mm, compaction settings ranging from about 0 to about 5 mm, and speeds from about 60,000 capsules per hour to about 130,000 capsules per hour. Weight control of the dose was observed to decrease with either (i) low speed and high compaction, or (ii) high speed and high bed heights. Accordingly, these combinations of parameters preferably are carefully controlled. It has also been discovered that slug formation can be minimized or eliminated by using the lowest compaction setting at which capsule weight control can be maintained. Where coated tablets are desired, conventional coating techniques known to those of ordinary skill in the art can be employed.

This combination of unit operations produces granules that are uniform in celecoxib content at the unit dose level, that readily disintegrate, that flow with sufficient ease so that weight variation can be reliably controlled during capsule filling or tableting, and that are dense enough in bulk so that the batch can be processed in the selected equipment and individual doses fit into the specified capsules or tablet dies.

Use in the Preparation of Medicaments

The present invention also is directed to use of compositions of the present invention in preparation of medicaments useful in the treatment and/or prophylaxis of cyclooxygenase-2 mediated conditions and disorders.

EXAMPLES

The following examples illustrate aspects of the present invention but should not be construed as limitations. The experimental procedures used to generate the data shown are discussed in more detail below. The symbols and conventions used in these examples are consistent with those used in the contemporary pharmaceutical literature. Unless otherwise stated, (i) all percentages recited in these examples are by weight based on total composition weight, (ii) total composition weight for capsules is the total capsule fill weight and does not include the weight of the actual capsule employed, and (iii) coated tablets are coated with a conventional coating material such as Opadry White YS-1-18027A and the weight fraction of the coating is about 3% of the total weight of the coated tablet.

Example 1: 100 mg Dose Capsule

A capsule was prepared having the following composition:

TABLE 1

| Ingredient | Weight fraction (%) | Amount (mg) |
| --- | --- | --- |
| Celecoxib | 37.04 | 100 |
| Lactose monohydrate (NF, Ph Eur) | 55.46 | 149.75 |
| Sodium lauryl sulfate (NF, Ph Eur) | 3 | 8.1 |

TABLE 1-continued

| Ingredient | Weight fraction (%) | Amount (mg) |
|---|---|---|
| Povidone (K29-32 USP) | 2.5 | 6.75 |
| Croscarmellose sodium (NF, Ph Eur) | 1 | 2.7 |
| Magnesium stearate (NF, Ph Eur) | 1 | 2.7 |
| Total capsule fill weight | 100 | 270 |

The above unit dose composition was placed in a hard gelatin capsule (white opaque, size #2) comprising titanium dioxide (USP), gelatin (NF), and blue ink (SB-6018).

The lactose monohydrate used in each of the examples herein is commercially available from Formost Farms, Baraboo, Wis. The Ac-Di-Sol brand of croscarmellose sodium used in each of the examples herein is commercially available from FMC Corporation, Chicago, Ill. The sodium lauryl sulfate used in each of the examples herein is commercially available from Henkel Corporation, Cincinnati, Ohio. The povidone (polyvinylpyrrolidone) used in each of the examples herein is commercially available from International Specialty Products. The magnesium stearate used in each of the examples herein is commercially available from Mallinckrodt Inc., St. Louis, Mo. The Opadry White YS-1-18027A used to prepare the coated tablets disclosed in the examples of this application is a ready-to-coat coating formulation commercially available from Colorcon, West Point, Pa.

Capsule doses of any desired strength from 25 mg to 225 mg can be accommodated by adjusting the weight of celecoxib and correspondingly increasing or decreasing the amount of lactose as necessary to provide a total fill weight of 270 mg.

Example 2: 200 mg Dose Capsule

A capsule was prepared having the following composition:

TABLE 2

| Ingredient | Weight fraction (%) | Amount (mg) |
|---|---|---|
| Celecoxib | 74.07 | 200 |
| Lactose monohydrate (NF, Ph Eur) | 18.43 | 49.75 |
| Sodium lauryl sulfate(NF, Ph Eur) | 3 | 8.10 |
| Povidone (K29-32 USP) | 2.5 | 6.75 |
| Croscarmellose sodium | 1 | 2.7 |
| Magnesium stearate (NF, Ph Eur) | 1 | 2.7 |
| Total capsule fill weight | 100 | 270 |

The above unit dose composition was placed in a hard gelatin capsule (white opaque, size #2) comprising titanium dioxide (USP), gelatin (NF), and blue ink (SB-6018).

Example 3: 100 mg Dose Tablet

Tablets were prepared having the following composition:

TABLE 3

| Ingredient | Amount/tablet (mg) | Weight fraction (%) | Amount/batch (kg) |
|---|---|---|---|
| Celecoxib | 100 | 40 | 6.40 |
| Lactose monohydrate (NF) | 101.88 | 40.75 | 6.52 |
| Sodium lauryl sulfate (NF) | 7.5 | 3 | 0.48 |
| Povidone (K29/32, USP) | 6.25 | 2.5 | 0.40 |
| Croscarmellose sodium (Type A, NF) | 7.5 | 3 | 0.48 |
| Microcrystalline cellulose (Avicel PH-102, NF) | 25 | 10 | 1.60 |
| Magnesium stearate (NF) | 1.88 | 0.75 | 0.12 |
| Total | 250.01 | 100 | 16 |
| Opadry White YS-1-18027A | 7.50 | | |

The tablets prepared were 0.210 inch×0.465 inch (5.0 mm×11.2 mm) modified oval shaped tablets.

The Avicel brand of microcrystalline cellulose was used in the preparation of the tablets of Examples 3 and 4 and is commercially available from FMC Corporation, Philadelphia, Pa.

Tablet dose strengths between 25 mg to 225 mg can be accommodated by increasing or decreasing the amounts of celecoxib and each of the carrier materials described above so as to maintain the same weight fractions exemplified above.

Example 4: 200 mg Dose Tablet

Tablets were prepared having the following composition:

TABLE 4

| Ingredient | Amount/tablet (mg) | Weight fraction (%) | Amount/batch (kg) |
|---|---|---|---|
| Celecoxib | 200 | 40 | 6.40 |
| Lactose monohydrate (NF) | 203.75 | 40.75 | 6.52 |
| Sodium lauryl sulfate (NF) | 15 | 3 | 0.48 |
| Povidone (K29/32, USP) | 12.5 | 2.5 | 0.40 |
| Croscarmellose sodium (Avicel PH-102, NF) | 15 | 3 | 0.48 |
| Microcrystalline cellulose (Type A, NF) | 50 | 10 | 1.60 |
| Magnesium stearate (NF) | 3.75 | 0.75 | 0.12 |
| Total | 500 | 100 | 16 |
| Opadry White YS-1-18027A | 15.0 | | |

The tablets prepared were 0.275 inch×0.496 inch (6.6 mm×11.9 mm) modified capsule shaped tablets.

Example 5: Disintegration Tests

Tablets were prepared as in Examples 3 and 4 except that they were left uncoated. Six identical tablets were separately placed into one of six tubes having a wire mesh screen bottom in a disintegration basket. A water bath was preheated to 37° C.±2° C. and maintained at that temperature for the duration of the disintegration test. A 1000 ml beaker was placed in the water bath. The beaker was filled with a sufficient amount of water to ensure that the wire mesh screen of the tubes would remain at least 2.5 cm below the water surface during the test. The disintegration basket was inserted in the water and repeatedly raised and lowered until the test was complete while maintaining the wire mesh screen of the tubes at least 2.5 cm below the water surface. Disintegration time for each tablet was the time, measured from time of insertion of the basket, at which the very last portion of the tablet passed through the screen at the bottom of the tube. The mean results for the uncoated tablets of Examples 3 and 4 are reported in Table 5.

TABLE 5

| Tablet | Disintegration time |
|---|---|
| Example 3: 100 mg dose tablet (uncoated) | 4 minutes 35 seconds |
| Example 4: 200 mg dose tablet (uncoated) | 7 minutes 40 seconds |

Example 6: Dissolution Tests

The apparatus of USP method 2 (with paddles) was used to determine the dissolution rate of the capsules of Examples 1 and 2 and the tablets of Examples 3 and 4, which for the purpose of these tests were left uncoated. A 1% sodium lauryl sulfate/0.04M $Na_3PO_4$ (pH=12) solution, 1000 ml, was used as the dissolution fluid. The solution was maintained at a temperature of 37° C.±5° C. and stirred at 50 rpm during the test. Twelve identical tablets or capsules were tested. The 12 tablets or capsules were each separately placed in one of 12 standard dissolution vessels, and at each of 15, 30, 45 and 60 minutes later, a 5 ml aliquot of solution was removed from each vessel. The sample from each vessel was filtered and the absorbance of the sample measured (UV spectrophotometer; 2 mm pathlength quartz cell; 243 nm or wavelength of UV maxima; blank: dissolution medium). Percent dissolution was calculated based on the measured absorbances. The mean results of the dissolution tests are reported in Table 6. Note that solubility at the elevated pH of these test conditions is not indicative of solubility in the gastrointestinal tract.

TABLE 6

| | % Dissolved | | | |
|---|---|---|---|---|
| Composition | 15 minutes | 30 minutes | 45 minutes | 60 minutes |
| Example 1: 100 mg capsule | 89 | 99 | 100 | 100 |
| Example 2: 200 mg capsule | 55 | 82 | 89 | 92 |
| Example 3: 100 mg tablet | 81 | 93 | 94 | 95 |
| Example 4: 200 mg tablet | 60 | 96 | 98 | 98 |

Example 7: Particle Size Analysis

Table 7A shows the results of a particle size sieve analysis of the wet granulated pharmaceutical compositions of Examples 1 and 2, respectively, prior to encapsulation. "Percent retained on screen" means the percentage by weight of the total batch having a particle size larger than the indicated sieve size.

TABLE 7A

| | Percent retained on screen | | | |
|---|---|---|---|---|
| | Example 1: 100 mg capsule | | Example 2: 200 mg capsule | |
| Sieve size (µm) | Lower limit | Upper limit | Lower limit | Upper limit |
| 850 | 0 | 1.3 | 1.1 | 10.7 |
| 425 | 2.8 | 14.9 | 4.3 | 25.4 |
| 250 | 10.0 | 25.5 | 10.8 | 35.4 |
| 180 | 15.3 | 39.0 | 17.3 | 39.2 |
| 106 | 32.5 | 64.5 | 35.2 | 58.2 |
| 75 | 37.1 | 77.5 | 39.5 | 71.8 |
| 0 | 100 | 100 | 100 | 100 |

Table 7B shows the results of a particle size sieve analysis of the wet granulated pharmaceutical compositions of Examples 3 and 4, respectively, prior to compression into the tablets. "Percent of batch" means the percentage by weight of the total batch having a particle size between the indicated sieve size and the next smaller sieve size indicated. "Cumulative percent of batch" reports the percentage by weight of the total batch having a particle size larger than the indicated sieve size.

TABLE 7B

| | Example 3: 100 mg tablet | | Example 4: 200 mg tablet | |
|---|---|---|---|---|
| Sieve size (µm) | Percent of batch | Cumulative percent of batch | Percent of batch | Cumulative percent of batch |
| 840 (20 mesh screen) | 1 | 1 | 0.79 | 0.79 |
| 420 (40 mesh screen) | 24.6 | 25.6 | 24.85 | 25.64 |
| 250 (60 mesh screen) | 18.4 | 44 | 19.13 | 44.77 |
| 177 (80 mesh screen) | 9.6 | 53.6 | 11.05 | 55.82 |
| 149 (100 mesh screen) | 6.6 | 60.2 | 6.9 | 62.72 |
| 105 (140 mesh screen) | 11.6 | 71.8 | 11.44 | 74.16 |
| 74 (200 mesh screen) | 8.8 | 80.6 | 8.28 | 82.45 |
| Fines | 19.4 | 100 | 17.55 | 100 |

Example 8: Bulk Density Analysis

Table 8 shows the results of a bulk density analysis of the wet granulated pharmaceutical compositions of Examples 1, 2, 3 and 4 prior to encapsulation or compression into tablets.

TABLE 8

| Composition | Bulk density (g/ml) | Tapped density (g/ml) | Loss on drying (%) |
|---|---|---|---|
| Example 1: 100 mg capsule | 0.77 | 1.02 | 0.6 |
| Example 2: 200 mg capsule | 0.61 | 0.96 | 0.5 |
| Example 3: 100 mg tablet | 0.73 | 0.87 | 1.37 |
| Example 4: 200 mg tablet | 0.72 | 0.86 | 1.4 |

Example 9: Tablet Analysis Program

Table 9 shows the results of a tablet analysis program ("TAP analysis") for a sampling of 10 tablets having the composition of the tablets of each of Examples 3 and 4.

TABLE 9

| Tablet | Average weight (mg) | Average thickness (mm) | Hardness (kP) |
|---|---|---|---|
| Example 3: 100 mg tablet | 248 | 3.85 | 8.2 |
| Example 4: 200 mg tablet | 500 | 5.22 | 14.6 |

Example 10: Friability Test

Tablets collectively weighing 12 g were placed in a rotating drum. Extraneous dust was first removed from the drum and the tablets. The drum was started and rotation continued for ten minutes at a minimum of 25 rpm. The rotation of the drum was stopped and the tablets removed. Loose dust on the tablets as well as any broken tablets were removed and the intact tablets were weighed. The percent loss of the test samples from the tablets of Examples 3 and 4 was calculated and is reported below in Table 10.

TABLE 10

| Tablet | Percent loss |
|---|---|
| Example 3: 100 mg tablet | 0.33 |
| Example 4: 200 mg tablet | 0.16 |

Example 11-1: Bioavailability in a Dog Model

Healthy female beagle dogs weighing 9 to 13 pounds (4.1 to 5.9 kg) received the following single doses of celecoxib: (1) an intravenous infusion of 0.5 mg/kg body weight of celecoxib followed by a second intravenous infusion of 5.0 mg/kg body weight of celecoxib; (2) 5 mg/kg body weight celecoxib in the form of an oral solution; and (3) 5.0 mg/kg body weight of neat unformulated celecoxib in the form of an oral capsule. The vehicle for the intravenous and oral solution doses was a mixture of polyethylene glycol having an average molecular weight of 400 (PEG-400) and water in a ratio of 2:1 by volume. Each intravenous infusion was given over a period of 15 minutes with 15 to 30 minutes separating the two infusions.

Multiple blood samples were collected from each animal by venipuncture or indwelling catheter into heparinized tubes. Celecoxib concentration in blood serum was measured by HPLC and the resulting data were used to calculate the pharmacokinetic parameters presented in Table 11-1 below.

TABLE 11-1

| Pharmacokinetic parameter | Intravenous infusion | Oral solution | Capsule, unformulated |
|---|---|---|---|
| $C_{max}$ (ng/ml) | 6950 | 2190 | 517 |
| $T_{max}$ (h) | Not applicable | 0.5 | 3.0 |
| $AUC_{0-\infty}$ (ng/ml)h | 31200 | 16200 | 4800 |
| Clearance (ml/min · kg) | 3.08 | 5.14 | 17.4 |
| $T_{1/2}$ (h) | 8.84 | 9.15 | 11.8 |
| Bioavailability (%) | Not applicable | 57.1 | 16.9 |

Example 11-2: Relative Bioavailability of Formulations in a Dog Model

The effect of such formulation parameters as celecoxib particle size, increased concentration of wetting agent, pH, and dispersion of celecoxib as a suspension were evaluated relative to an oral solution on bioavailability in a dog model. The effect of micronizing the celecoxib (mean particle size 10-20 μm) prior to formulating was tested in composition A. The combined effect of micronization, added wetting agent (sodium lauryl sulfate), and increased micro-environmental pH ($Na_3PO_4.12H_2O$) was tested in composition B. The effect of bringing wetting agent (Tween 80) into intimate contact with celecoxib (co-precipitating vs. simple dry mixing) was tested in composition C. The effect of further reducing particle size (approximating 1 μm) and dispersing the particles in a suspension was tested in composition D. A solution of celecoxib similar to that used in Example 11-1 (composition E) was included as a reference. In addition, data from Example 11-1 for unmilled, unformulated celecoxib in a capsule (composition F) is also included as a reference. The specific compositions of formulations A, B, C, D, E and F are summarized in Table 11-2A.

TABLE 11-2A

| | Weight fraction (% dry basis) | | | | | |
|---|---|---|---|---|---|---|
| Ingredient | A | B | C | D | E | F |
| celecoxib (micronized) | 25 | 25 | | | | |
| celecoxib/tween 80[1] | | | 25 | | | |
| celecoxib (dispersed)[2] | | | | 100 | | |
| celecoxib (solution)[3] | | | | | 100 | |
| celecoxib (unmilled) | | | | | | 100 |
| sodium lauryl sulfate | 2 | 25 | | | | |
| Avicel 101 | 73 | 25 | 75 | | | |
| $Na_3PO_4H_2O$ | | 25 | | | | |
| Total | 100 | 100 | 100 | 100 | 100 | 100 |

[1]Precipitated from ethanol solution using an aqueous solution of 5% polysorbate 80 as an antisolvent.
[2]Prepared as a suspension by ball-milling the drug in a slurry of polysorbate 80 and polyvinylpyrollidone until particles were approximately 1 μm in diameter as estimated by microscopy.
[3]Solution in PEG-400/water (2:1 v/v).

The compositions were administered to groups of three male and three female dogs. Group 1 dogs were administered 5 mg per kg body weight celecoxib in solution E and in capsule formulations A and B in a nonrandomized crossover design. Group 2 dogs were administered 5 mg per kg body weight celecoxib in capsule formulation C and in suspension D in a nonrandomized crossover design. Plasma samples were collected over a 24-hour period and analyzed for celecoxib by HPLC.

The results of the study (Tables 11-28, 11-2C and 11-2D) indicated that decreasing the particle size (composition A) or co-precipitating the celecoxib with a wetting agent (composition C) increased the bioavailability (as measured by $AUC_{(0-24)}$) of celecoxib compared to the earlier study of unformulated celecoxib shown in Example 11-1. The bioavailability of celecoxib was greater from the PEG-400/water solution (composition E) and the suspension (composition D). The bioavailability from the suspension having approximately 1 μm particle size was similar to that from the solution and provided strong indication that celecoxib availability from wet granulated solid compositions can be improved by reduced celecoxib particle size (for example by pin milling of celecoxib prior to formulation), increased wetting of the celecoxib (for example by including sodium lauryl sulfate in the granulating fluid) and improved dispersibility (for example by including croscarmellose sodium in the granulation). The bioavailability data contained in Tables 11-2C and 11-2D for each formulation represent the bioavailability of that formulation as a percent of the bioavailability experimentally measured for intravenous administration of celecoxib, using the solution (composition E) data as a bridge between the studies of Examples 11-1 and 11-2.

TABLE 11-2B

| Time (h) | Blood serum celecoxib concentration (μg/ml) | | | | | |
|---|---|---|---|---|---|---|
| | A | B | C | D | E | F |
| 0 | 0 | 0 | 0 | 0 | 0 | 0 |
| 0.5 | 0.0143 | 0.247 | 0.0635 | 0.453 | 0.824 | 0.205 |
| 1.0 | 0.244 | 0.228 | 0.443 | 0.826 | 0.820 | 0.333 |
| 2.0 | 0.318 | 0.138 | 0.717 | 0.865 | 0.604 | 0.262 |
| 3.0 | 0.189 | 0.0860 | 0.492 | 0.741 | 0.517 | 0.517 |
| 4.0 | 0.145 | 0.0707 | 0.384 | 0.576 | 0.413 | 0.234 |
| 6.0 | 0.107 | 0.0664 | 0.233 | 0.354 | 0.286 | — |
| 7.0 | — | — | — | — | — | 0.197 |
| 8.0 | 0.0828 | 0.0624 | 0.160 | 0.234 | 0.187 | — |
| 12.0 | 0.0939 | 0.0431 | 0.0865 | 0.142 | 0.0802 | — |
| 24.0 | — | 0.0404 | 0.0408 | 0.0394 | 0.0159 | — |

TABLE 11-2C

| Pharmacokinetic parameter | Value for female dogs | | | | | |
|---|---|---|---|---|---|---|
| | A | B | C | D | E | F |
| $C_{max}$ (ng/ml) | 360 ± 60 | 250 ± 70 | 790 ± 190 | 1010 ± 270 | 840 ± 240 | 500 |
| $T_{max}$ (h) | 1.3 ± 0.2 | 0.7 ± 0.2 | 1.5 ± 0.3 | 1.7 ± 0.44 | 0.67 ± 0.18 | 3.0 |
| Bioavailability (%) | 31.2 ± 2.9 | 24.9 ± 1.4 | 46.3 ± 9.5 | 69.5 ± 9.6 | 62.4 ± 9.4 | 16.9 |

TABLE 11-2D

| Pharmacokinetic parameter | Value for male dogs | | | | | |
|---|---|---|---|---|---|---|
| | A | B | C | D | E | F |
| $C_{max}$ (ng/ml) | 520 ± 110 | 450 ± 180 | 640 ± 260 | 830 ± 330 | 1520 ± 200 | 500 |
| $T_{max}$ (h) | 5.3 ± 3.3 | 3.3 ± 1.3 | 1.5 ± 0.5 | 5.7 ± 3.42 | 1.5 | 3.0 |
| Bioavailability (%) | 49.4 ± 12.0 | 54.2 ± 13.1 | 42.9 ± 13.1 | 87.5 ± 20.6 | 89.4 ± 4.5 | 16.9 |

Example 11-3

Various formulations containing sodium lauryl sulfate (0-5% by weight) and croscarmellose sodium (0-5% by weight) were screened for relative wettability and disintegration tendency. Relative wettability was estimated by measuring the time required for water to penetrate a column of granulated material prepared from each formulation. Disintegration tendency was determined by measuring the weight of granulated material retained on a 20 mesh (850 mm) screen after soaking the material in 37° C. water for 5 minutes. The specific compositions of compositions A through H evaluated are summarized in Table 11-3A,

TABLE 11-3A

| | Weight fraction (%) | | | | | | | |
|---|---|---|---|---|---|---|---|---|
| Composition | A[1] | B | C | D | E | F | G | H |
| Celecoxib | 74.7 | 74.7 | 74.7 | 74.7 | 74.7 | 74.7 | 74.7 | 74.7 |
| Lactose | 15.8 | 15.8 | 21.8 | 19.8 | 17.8 | 15.8 | 17.8 | 11.8 |
| Polyvinyl-pyrrolidone | 2.5 | 2.5 | 2.5 | 2.5 | 2.5 | 2.5 | 2.5 | 2.5 |
| Sodium lauryl sulfate | 3.0 | 3.0 | 0.0 | 1.0 | 1.0 | 1.0 | 3.0 | 5.0 |
| Ac-di-sol | 3.0 | 3.0 | 0.0 | 1.0 | 3.0 | 5.0 | 1.0 | 5.0 |

TABLE 11-3A-continued

| | Weight fraction (%) | | | | | | | |
|---|---|---|---|---|---|---|---|---|
| Composition | A[1] | B | C | D | E | F | G | H |
| Magnesium stearate | 1.0 | 1.0 | 1.0 | 1.0 | 1.0 | 1.0 | 1.0 | 1.0 |

[1]Sodium lauryl sulfate was added as a dry powder

Results are summarized in Table 11-3B. Penetration tests were done in triplicate. Disintegration tests were done in duplicate. Results of the penetration study indicated that wet application of sodium lauryl sulfate (Composition B) was superior to dry application (Composition A) and that formulations containing 3% to 5% sodium lauryl sulfate (Compositions B, G and H) were superior to those with lesser amounts of sodium lauryl sulfate (Compositions C through F). Formulations containing 3% sodium lauryl sulfate (Compositions B and G) were similar to those containing 5% sodium lauryl sulfate (Composition H). Results of the disintegration study indicated that complete disintegration could be achieved with sodium crosscarmellose concentrations as low as 1% (Composition G) at a wetting agent concentration of 3%. Complete disintegration could also be achieved with higher amounts of disintegrant (Compositions B, F and H) regardless of wetting agent concentration. Composition G exhibited both superior penetration and complete disintegration with the minimum amount of excipient required.

TABLE 11-3B

| Composition | % Sodium lauryl sulfate/ % Ac-di-sol | Penetration time | Disintegration |
|---|---|---|---|
| A | 3/3 | >18 hours | 0.1-0.5% |
| B | 3/3 | 5-60 minutes | none detected |
| C | 0/0 | >4 to >18 hours | 20-26% |
| D | 1/1 | >4 to >18 hours | 10-13% |
| E | 1/3 | 2 to 4 hours | 4-6% |
| F | 1/5 | 1 to 4 hours | none detected |
| G | 3/1 | 10 to 40 minutes | none detected |
| H | 5/5 | 10 to 55 minutes | none detected |

Example 12

The following formulations were evaluated for wetting effects and mixture uniformity:

TABLE 12

| Ingredient | Weight fraction (%) | | | | | | | |
|---|---|---|---|---|---|---|---|---|
| | Lactose dry blend | | Microcrystalline cellulose dry blend | | Polyvinyl-pyrrolidone granulation[1] | | Polysorbate 80 granulation[2] | |
| Celecoxib | 5 | 60 | 5 | 60 | 5 | 60 | 5 | 60 |
| Lactose | 94.5 | 39.5 | — | — | 92 | 37 | 93.5 | 38.5 |
| Microcrystalline cellulose | — | — | 94.5 | 39.5 | — | — | — | — |
| Polysorbate 80 | — | — | — | — | — | — | 1.0 | 1.0 |
| Povidone (K29-32) | — | — | — | — | 2.5 | 2.5 | — | — |
| Magnesium stearate | 0.5 | 0.5 | 0.5 | 0.5 | 0.5 | 0.5 | 0.5 | 0.5 |

[1] In this formulation polyvinylpyrrolidone was added to the blend as a dry powder prior to granulation with water.
[2] In this formulation celecoxib and lactose were granulated with an aqueous solution of polysorbate 80.

The 5% celecoxib blends exhibited better blend homogeneity than the 60% celecoxib blends. The measured relative standard deviations for the 5% celecoxib blends ranged from 0.4% to 3.5% while the measured relative standard deviations for the 60% celecoxib blends ranged from 4.7% to 6.3%. In addition to being less homogeneous, the 60% celecoxib blends contained relatively large granules (greater than 420 μm) that were superpotent (containing 124% to 132% higher concentrations of celecoxib relative to other granules).

Four similar formulations were prepared containing 25% celecoxib loading instead of 5% or 60% celecoxib loading as above. The bioavailability of these formulations was evaluated in a dog model, by a procedure similar to that outlined for Examples 11-1 and 11-2. The polyvinylpyrrolidone wet granulation formulation exhibited the highest bioavailability (about 74%).

Example 13

Capsules having the following formulations were prepared and evaluated:

TABLE 13A

| Ingredient | Amount (mg) | | |
|---|---|---|---|
| | 5 mg capsule | 20 mg capsule | 100 mg capsule |
| Celecoxib | 5 | 20 | 100 |
| Lactose | 92 | 77 | 61.9 |
| Povidone (K29-32) | 2.5 | 2.5 | 4 |
| Magnesium stearate | 0.5 | 0.5 | 0.8 |
| Total | 100 | 100 | 166.7 |
| Capsule shell | 1 | 1 | 1 |
| Capsule size | #3 | #3 | #3 |

The celecoxib was milled by multiple passes through an oscillating mill fitted with successively smaller screen sizes (#14, #20, #40). The $D_{90}$ particle size of the celecoxib particles added to this mixture was less than about 37 Celecoxib, lactose and polyvinylpyrrolidone were mixed in a planetary mixer bowl and wet-granulated with water. The granulation was then tray dried at 60° C., milled through a 40 mesh screen, lubricated with magnesium stearate in a V-blender and encapsulated on a dosator-type encapsulator. The in vitro dissolution profile of the capsules was determined using USP method 2 and a 15 mM phosphate buffer at pH 10 as dissolution medium. About 50% in vitro dissolution was achieved after about 15 minutes with greater than 95% in vitro dissolution after about 30 minutes.

The absorption, distribution, metabolism and elimination profile of this 100 mg unit dose capsule was compared to the profile of a suspension of $^{14}$C-celecoxib. The study was an open-label, randomized crossover study carried out in ten healthy male subjects. The suspension was prepared by dissolving celecoxib in ethanol containing 5% polysorbate 80 and adding that mixture to apple juice prior to administration. Subjects receiving the suspension ingested a 300 mg dose of celecoxib. Subjects receiving capsule-form celecoxib received three 100 mg unit dose capsules for a total dose of 300 mg of celecoxib. The rate of absorption from the capsule was slower than from the suspension, but was equivalent to the suspension when measured by $AUC_{0-48}$. Mean results are reported in Table 13B below. Celecoxib was largely metabolized with only about 2.56% of the radioactive dose in either urine or feces.

TABLE 13B

| Pharmacokinetic parameter | Suspension | Capsules |
|---|---|---|
| $AUC_{(0-48)}$ ((ng/ml)h) | 8706.7 | 8763.1 |
| $C_{max}$ (ng/ml) | 1526.5 | 1076.5 |
| $T_{max}$ (h) | 1.42 | 1.94 |
| $T_{1/2}$ (h) | 11.53 | 15.57 |

Example 14

Capsules having the following compositions were prepared and evaluated:

TABLE 14

| Ingredient | Amount (mg) | |
|---|---|---|
| | 100 mg capsule | 200 mg capsule |
| Celecoxib | 100 | 200 |
| Lactose | 223.4 | 120.1 |
| Povidone (K29-32) | 8.3 | 8.3 |
| Magnesium stearate | 1.7 | 5 |
| Total | 333.4 | 333.4 |
| Capsule size | #1 | #1 |

These formulations were prepared in a manner similar to the formulations of Example 13 except that an inpact-type pin mill was used instead of an oscillating mill. Particle size was further reduced by use of the pin mill. For the 100 mg capsule about 30% in vitro dissolution was achieved after about 15 minutes with greater than 85% in vitro dissolution after about 30 minutes. For the 200 mg capsule about 50% in vitro dissolution was achieved after about 15 minutes with greater than 85% in vitro dissolution after about 30 minutes.

Example 15: Preparation of 100 mg Dose Capsules

Figure 2:
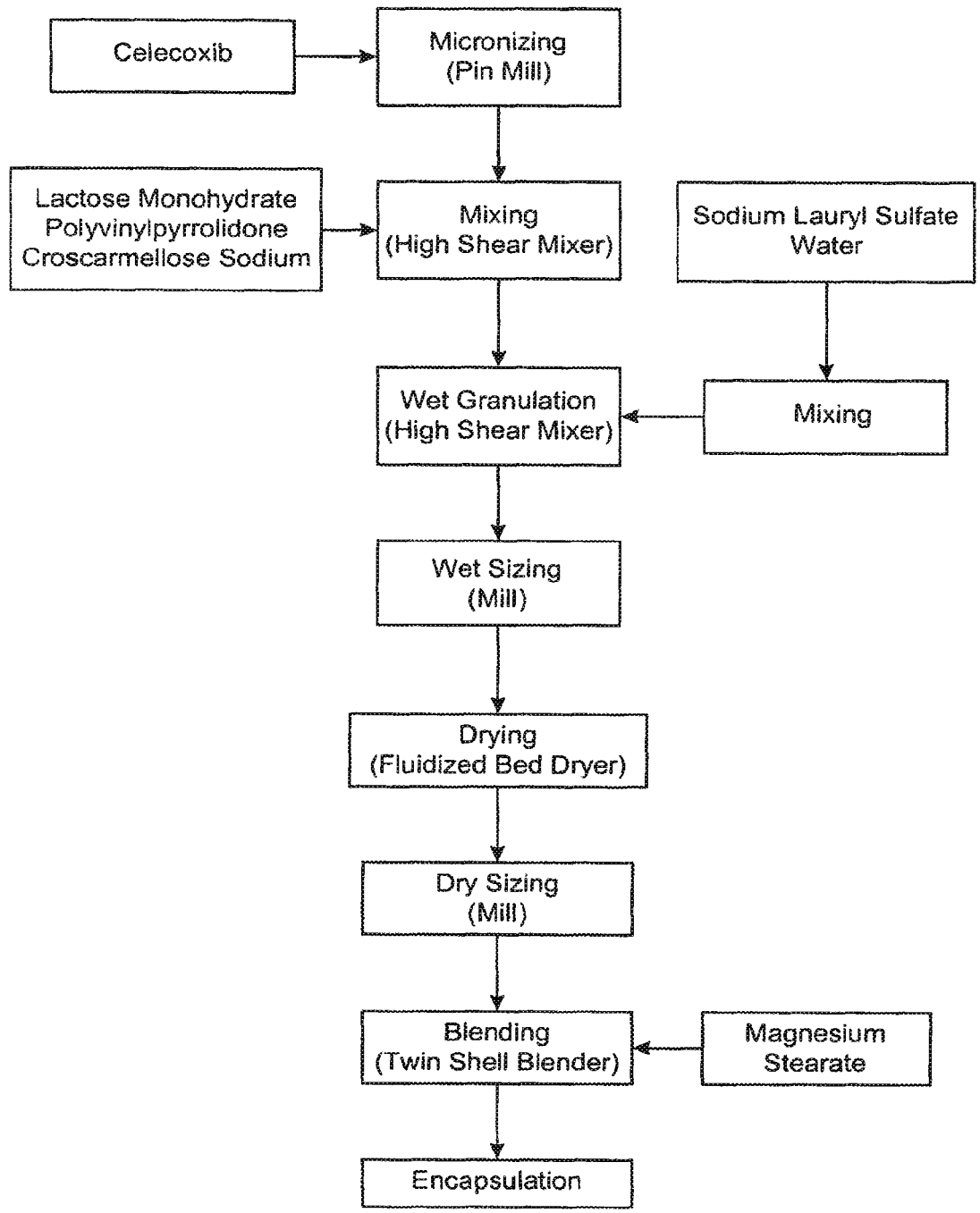
FIG. 2 is a flow diagram illustrating an alternative method for the preparation of pharmaceutical compositions of the present invention in the form of capsules.

Capsules providing a 100 mg or 200 mg dose of celecoxib, and having the composition shown in Examples 1 or 2 respectively, can be prepared in accordance with acceptable pharmaceutical manufacturing practices in the manner illustrated by FIG. 1 or FIG. 2. Tablets provising a 100 mg or 200 mg dose of celecoxib, and having the composition shown in Examples 3 or 4 respectively, can be prepared by appropriately modifying the process of FIG. 1 or FIG. 2 to account for the extragranular addition of croscarmellose sodium and microcrystalline cellulose, and tableting instead of encapsulating the composition.

In an illustrative process for the bulk formulation of 100 mg dose capsules using the starting materials described below, a typical batch consists of four identical granulation sections, although the number of granulation sections is not narrowly critical and depends largely upon equipment handling capacity and batch size needed.
Milling.

The celecoxib was milled in an impact-type pin mill with counter rotating disks. At mill speeds ranging from about 8960 rpm/5600 rpm to about 11200 rpm/5600 rpm (rotating rpm/counter-rotating rpm), particle size varied within relatively narrow ranges ($D_{90}$ of 30 µM or less) suggesting that mill speed is not narrowly critical to the bulk drug micronization process. FIG. 2 is a flow diagram showing a preferred embodiment wherein the celecoxib starting material is impact milled, preferably with a pin mill, prior to blending with the carrier materials.
Dry Mixing.

The celecoxib, lactose, polyvinylpyrrolidone and croscarmellose sodium were transferred to a 1200 L Niro Fielder PMA-1200 high speed granulator and mixed for about 3 minutes at fast chopper and impeller speeds. This dry mixing time provided adequate mixing of celecoxib with the carrier materials prior to the start of the wet granulation step.
Wet Granulation.

Sodium lauryl sulfate (8.1 kg) was dissolved in purified USP water (23.7 kg). The resulting solution was progressively added to the granulator at a rate of about 14 kg/minute. Total granulation time was about 6.5 minutes. During this granulation, the main blade and chopper blade of the granulator were placed on the fast speed setting. The wet granulated mixture contained about 8.1% water by weight. Alternatively, the sodium lauryl sulfate can be mixed with the celecoxib, lactose, polyvinylpyrrolidone and croscarmellose sodium in the dry mixing step and purified USP water can be added to this dry mixture comprising sodium lauryl sulfate.
Drying.

The product of the wet granulation operation was delumped using a Quadro Comil Model 198 S screening mill equipped with rotating impeller and a coarse screen. Wet milling was used to eliminate large material lumps that formed as a by-product of the wet granulation operation. If not removed, these lumps would have prolonged the subsequent fluidized bed drying operation and increased the variation with respect to moisture control. The delumped granules were transferred to an Aeromatic Fluid Bed Dryer T-8. The inlet air temperature and flow rate were adjusted to about 60° C. and about 5000 to 6000 ft$^3$/minute (about 140 to 170 m$^3$/minute). The granules were dried in the fluidized bed dryer to reduce the moisture content to 0.5% to 2.5%. Moisture content was monitored using a Computrac Moisture Analyzer. Drying continued until the loss on drying of the granulation was not more than 1.0%. It may be desirable to combine two or more granulation sections for this drying step and subsequent processing steps.
Dry Milling.

The dry granules were passed through a Fluid Air Mill Model 007 impact (conventional hammer) mill equipped with a 0.028 inch to 0.063 inch (0.7 mm to 1.5 mm) screen, knives forward, and operated at 2400 rpm speed. Dry milling was used in combination with the wet granulation step to control the final size distribution of the granules.
Blending and Lubrication.

The milled granules were then placed in a PK Cross-Flow Blender 75 Cubic Foot diffusion mixer/V-blender. The magnesium stearate was added and the mixture blended for about 5 minutes. The blending time provided blended material that was uniform with respect to the concentration of celecoxib. Blender rotational speed was 10.6 revolutions per minute. The final blend was used to combine materials from multiple granulation sections into a single uniform mixture and to evenly distribute lubricant into the material prior to encapsulation.
Encapsulation.

The granulated powder blend was encapsulated using an MG2 G100 or G120 encapsulator. The capsules were polished.

The above sequence of unit operations produced granules that were highly uniform in celecoxib content at the unit dose level, that readily dissolved in vitro, that flowed with sufficient ease so that weight variation could be reliably controlled during capsule filling, and that were dense enough in bulk so that the batch could be processed in the selected equipment and individual doses fit into the specified capsules.

Example 16: Bioequivalency Study

The bioequivalency and safety of 200 mg doses of celecoxib were evaluated in an open-label, randomized, single dose, three-way crossover study of a group of 46 healthy adult humans. The subjects received three single 200 mg doses of celecoxib administered as (A) one 200 mg dose capsule, (13) two 100 mg dose capsules, or (C) two 100 mg dose capsules (from a different batch run). Treatments were separated by seven days. The specific pharmaceutical compositions of the 100 mg dose capsule and the 200 mg dose capsules are disclosed in Examples 1 and 2, respectively. The subjects, who had fasted overnight, received single oral doses of the study medication together with about 180 ml of water at 0800 hours. The subjects continued to fast and remained in an upright position for four hours after dose administration. Blood samples were collected at −0.25 (pre-dose), 0.5, 1, 1.5, 2, 3, 4, 6, 8, 12, 16, 24, 36 and 48 hours post dose. Analyses of the separated plasma were performed at PPD Pharmaco, Richmond, Va. Celecoxib plasma concentrations were determined using a validated high performance liquid chromatography ("HPLC") procedure with a lower limit of detection of 10.0 ng/ml. Each subject was separately tested. A minimum seven day wash-out period was allowed between administration of each single 200 mg dose. The mean results obtained from the 46 subjects tested are reported in Tables 16A and 16B below.

TABLE 16A

| | Plasma celecoxib concentration (ng/ml) | | |
|---|---|---|---|
| Time (h) | One 200 mg capsule | Two 100 mg capsules (Batch 1) | Two 100 mg capsules (Batch 2) |
| −0.25 | 0.22 | 0.00 | 0.00 |
| 0.5 | 103.74 | 117.89 | 212.61 |
| 1.0 | 418.24 | 446.39 | 647.00 |
| 1.5 | 575.68 | 606.97 | 826.90 |
| 2.0 | 646.83 | 656.98 | 862.23 |
| 3.0 | 686.19 | 666.55 | 781.13 |
| 4.0 | 621.02 | 595.21 | 660.15 |
| 6.0 | 389.00 | 387.41 | 383.81 |
| 8.0 | 322.24 | 332.51 | 323.59 |
| 12.0 | 214.63 | 208.06 | 209.96 |
| 16.0 | 149.11 | 146.40 | 144.23 |
| 24.0 | 116.09 | 111.77 | 113.21 |
| 36.0 | 52.76 | 48.27 | 46.98 |
| 48.0 | 27.24 | 26.47 | 22.44 |

TABLE 16B

| | Value of pharmacokinetic parameter | | |
|---|---|---|---|
| Pharmacokinetic parameter | One 200 mg capsule | Two 100 mg capsules (Batch 1) | Two 100 mg capsules (Batch 2) |
| $AUC_{(0-48)}$ ((ng/ml)h) | 8107.07 | 7976.56 | 8535.49 |
| $AUC_{(0-LQC)}$ ((ng/ml)h) | 8063.17 | 7953.71 | 8501.94 |
| $AUC_{(0-\infty)}$ ((ng/ml)h) | 8828.64 | 8640.46 | 9229.52 |
| $C_{max}$ (ng/ml) | 801.19 | 815.21 | 959.50 |
| $T_{max}$ (h) | 2.46 | 2.84 | 2.23 |
| $T_{1/2}$ (h) | 12.22 | 13.52 | 10.67 |
| $C_{max}/AUC_{(0-LQC)}$ | 0.10 | 0.10 | 0.20 |

Example 17: Effect of Food Study

An open-label randomized, single dose, four-way crossover study was employed to evaluate the dose proportionality and the effect of food on the pharmacokinetic profile of celecoxib in healthy adult subjects. Safety was assessed based on adverse events, vital signs and clinical laboratory tests. Twenty four healthy adult subjects were randomized to receive the following single doses of celecoxib: (A) a 50 mg dose capsule under fasting conditions, (B) a 50 mg dose capsule immediately following a high fat breakfast, (C) a 100 mg dose capsule under fasting conditions, and (D) a 100 mg dose capsule immediately following a high fat breakfast. The subjects received the study medication on days 1, 8, 15 and 22 in one of four treatment sequences (ADBC; BACD; CBDA; and DCAB). The specific composition of the 100 mg dose capsule is disclosed in Example 1. The specific composition of the 50 mg dose capsule is disclosed in Table 17A below:

TABLE 17A

| Ingredient | Amount (mg) |
|---|---|
| Celecoxib | 50.00 |
| Lactose monohydrate | 199.8 |
| Sodium lauryl sulfate | 8.1 |
| Povidone (K29-32) | 6.8 |
| Croscarmellose sodium | 2.7 |
| Magnesium stearate | 2.7 |
| Total capsule fill weight | 270.0 |

The above unit dose composition was placed in a hard gelatin capsule (white opaque, size #2).

Blood samples were collected at −0.25 (predose), 0.5, 1, 1.5, 2, 3, 4, 6, 8, 12, 16, 24, 36 and 48 hours post dose. Analyses of the separated plasma were performed at PPD Pharmaco, Richmond, Va. Celecoxib plasma concentrations were determined using a validated high performance liquid chromatography ("HPLC") procedure with a lower limit of detection of 10.0 ng/ml. There were no clinically significant changes in vital signs or physical examinations. All adverse events were mild in severity. The mean results obtained from the 24 subjects tested are reported in Tables 17B and 17C below.

TABLE 17B

| | Plasma celecoxib concentration (ng/ml) | | | |
|---|---|---|---|---|
| Time (h) | 100 mg capsule (fasting) | 100 mg capsule (high fat breakfast) | 50 mg capsule (fasting) | 50 mg capsule (high fat breakfast) |
| −0.25 | 0.00 | 0.00 | 0.00 | 0.00 |
| 0.5 | 63.96 | 1.35 | 52.90 | 2.38 |
| 1.0 | 225.65 | 14.00 | 155.07 | 11.98 |
| 1.5 | 344.77 | 49.37 | 202.22 | 29.85 |
| 2.0 | 354.45 | 139.43 | 220.15 | 63.00 |
| 3.0 | 348.03 | 438.99 | 253.85 | 186.94 |
| 4.0 | 333.86 | 600.00 | 244.80 | 298.23 |
| 6.0 | 196.53 | 355.65 | 118.58 | 188.90 |
| 8.0 | 152.35 | 314.54 | 91.79 | 165.85 |
| 12.0 | 121.08 | 179.04 | 61.13 | 88.76 |
| 16.0 | 86.13 | 102.12 | 39.51 | 51.86 |
| 24.0 | 61.77 | 49.31 | 28.22 | 22.81 |
| 36.0 | 38.00 | 17.88 | 10.69 | 8.75 |
| 48.0 | 17.77 | 7.91 | 5.77 | 3.80 |

TABLE 17C

| | Value of pharmacokinetic parameter | | | |
|---|---|---|---|---|
| Pharmacokinetic parameter | 100 mg capsule (fasting) | 100 mg capsule (high fat breakfast) | 50 mg capsule (fasting) | 50 mg capsule (high fat breakfast) |
| $AUC_{(0-48)}$ ((ng/ml)h) | 4463.28 | 5214.86 | 2426.23 | 2601.10 |
| $AUC_{(0-LQC)}$ ((ng/ml)h) | 4415.59 | 5105.50 | 2352.68 | 2501.56 |
| $AUC_{(0-\infty)}$ ((ng/ml)h) | 5126.74 | 5419.21 | 2693.80 | 2759.42 |
| $C_{max}$ (mg/ml) | 455.00 | 746.96 | 321.46 | 354.17 |
| $T_{max}$ (h) | 2.60 | 5.00 | 2.92 | 4.46 |
| $T_{1/2}$ (h) | 16.02 | 6.86 | 11.01 | 6.49 |
| $C_{max}/AUC_{(0-LQC)}$ | 0.11 | 0.15 | 0.16 | 0.16 |

Example 18: Pharmacokinetics of Suspension Versus Capsule Formulation

The pharmacokinetics and bioavailability of an oral fine suspension and two oral capsules containing celecoxib were evaluated in an open-label, randomized, single dose, crossover study. Thirty six healthy adult subjects were randomized to receive the following single doses of celecoxib: (A)

one 200 mg dose capsule, (B) two 100 mg dose capsules, and (C) a 200 mg oral fine suspension. The entire treatment duration was 18 days. On days 1, 8 and 15 the subjects received one of the three treatments according to a randomization schedule. Treatments were separated by seven days. The specific pharmaceutical composition of the 200 mg dose capsule is disclosed in Example 2. The specific pharmaceutical composition of the 100 mg dose capsules is disclosed in Table 18A below.

TABLE 18A

| Ingredient | Amount (mg) | Weight % |
|---|---|---|
| Celecoxib | 100.0 | 60.0 |
| Lactose Monohydrate | 61.7 | 37.0 |
| Povidone, K29-32 | 4.20 | 2.51 |
| Magnesium Stearate | 0.80 | 0.48 |

The pharmaceutical composition used in the 100 mg dose capsules was prepared by passing the celecoxib starting material through a 40 mesh oscillating screen (no other milling was performed), wet granulating the celecoxib, lactose and povidone in a low shear planetary mixer, tray drying and milling the granulated mixture, adding magnesium stearate to the granulated mixture and blending to form the final pharmaceutical composition.

The oral fine suspension was prepared by dissolving celecoxib in ethanol containing 5% polysorbate 80 and adding that mixture to apple juice prior to administration.

Blood samples were collected at −0.25 (predose) and through 72 hours post dose. Each subject was separately tested after receiving the 200 dose mg capsule, 100 mg dose capsules and oral fine suspension. A minimum of a seven day wash-out period was allowed between administration of each 200 mg dose. The mean results obtained from the 36 subjects tested are reported in Table 18B below.

TABLE 18B

| Pharma-cokinetic parameter | Value of pharmacokinetic parameter | | |
|---|---|---|---|
| | Two 100 mg capsules | One 200 mg capsule | 200 mg oral fine suspension |
| $AUC_{(0-72)}$ ((ng/ml)h) | 7247.5 ± 2427.5 | 7648.1 ± 2412.1 | 7736.2 ± 2488.2 |
| $AUC_{(0-\infty)}$ ((ng/ml)h) | 7562.4 ± 2494.0 | 7830.3 ± 2448.4 | 8001.2 ± 2535.6 |
| $C_{max}$ (ng/ml) | 619.7 ± 249.4 | 704.6 ± 265.7 | 1228.8 ± 452.0 |
| $T_{max}$ (h) | 3.00 ± 0.99 | 2.83 ± 1.06 | 0.79 ± 0.32 |
| $T_{1/2}$ (h) | 13.96 ± 5.27 | 11.92 ± 3.60 | 13.33 ± 6.69 |
| $Clearance_{(0-72)}$ (l/h) | 30.4 ± 9.8 | 28.4 ± 7.8 | 28.1 ± 7.8 |

In general, the rate of celecoxib absorption (higher $C_{max}$ and shorter $T_{max}$) was greater for the oral fine suspension than for the capsules. The overall extent of celecoxib absorption for the oral fine suspension, however, as measured by $AUC_{(0-72)}$ or $AUC_{(0-\infty)}$, was similar to the overall extent of celecoxib absorption for the capsules.

As various changes could be made in the above formulations and methods without departing from the scope of the invention, it is intended that all matter contained in the above description be interpreted as illustrative and not in a limiting sense. All mentioned references are incorporated by reference as if here written.

What is claimed is:

1. A pharmaceutical composition comprising one or more orally deliverable dose units, each comprising particulate celecoxib in an amount of about 10 mg to about 1000 mg in intimate mixture with one or more pharmaceutically acceptable excipients, and having a distribution of celecoxib particle sizes such that $D_{90}$ of the particles is less than 200 um; said composition exhibiting upon oral administration a relative bioavailability not less than about 50% by comparison with an orally delivered solution containing celecoxib at the same dosage rate, wherein said excipients include:
   a. one or more pharmaceutically acceptable diluents in a total amount of about 5% to about 99% by weight of the composition;
   b. one or more pharmaceutically acceptable disintegrants in a total amount of about 0.2% to about 30% by weight of the composition;
   c. one or more pharmaceutically acceptable binding agents in a total amount of about 0.5% to about 25% by weight of the composition;
   d. one or more pharmaceutically acceptable wetting agents in a total amount of about 0.25% to about 15% by weight of the composition; and
   e. one or more pharmaceutically acceptable lubricants in a total amount of about 0.1% to about 10% by weight of the composition.

2. The composition of claim 1 wherein the amount of celecoxib in each dose unit is about 50 mg to about 800 mg.

3. The composition of claim 1 wherein the amount of celecoxib in each dose unit is about 75 mg to about 400 mg.

4. The composition of claim 1 wherein the amount of celecoxib in each dose unit is about 100 mg to about 200 mg.

5. A composition of claim 1 that is suitable, by oral administration to a subject of a dose unit once or twice a day, for providing therapeutically or prophylactically effective inhibition of cyclooxygenase-2.

6. A composition of claim 1 that is suitable, by oral administration to a subject of a dose unit once or twice a day, for treatment or prophylaxis of a cyclooxygenase-2 mediated condition or disorder.

7. A composition of claim 1 in the form of unit dosage capsules or tablets.

* * * * *